United States Patent [19]
Caimi et al.

[11] Patent Number: 5,908,975
[45] Date of Patent: Jun. 1, 1999

[54] ACCUMULATION OF FRUCTANS IN PLANTS BY TARGETED EXPRESSION OF BACTERIAL LEVANSUCRASE

[75] Inventors: Perry Gerard Caimi, Landenberg; Howard Paul Hershey, West Chester, both of Pa.; Phillip S. Kerr, Urbandale, Iowa

[73] Assignee: E. I. du Pont de Nemours and Company, Wilmington, Del.

[21] Appl. No.: 08/640,732
[22] PCT Filed: Nov. 7, 1994
[86] PCT No.: PCT/US94/12778
§ 371 Date: May 6, 1996
§ 102(e) Date: May 6, 1996
[87] PCT Pub. No.: WO95/13389
PCT Pub. Date: May 18, 1995

Related U.S. Application Data

[63] Continuation-in-part of application No. 08/149,689, Nov. 9, 1993, abandoned.
[51] Int. Cl.$^6$ .............................. A01H 5/00; A01H 5/10; C12N 5/14; C12N 15/31
[52] U.S. Cl. ...................... 800/298; 435/320.1; 435/419; 435/468; 536/23.2; 536/23.7; 800/317.2; 800/317.3; 800/320.1
[58] Field of Search ................................ 435/320.1, 419, 435/172.3, 468; 536/23.2, 23.7, 24.1; 800/205, 250, DIG. 42, DIG. 43, DIG. 56, 298, 317.2, 317.3, 320.1

[56] References Cited

U.S. PATENT DOCUMENTS

| | | | |
|---|---|---|---|
| 4,277,563 | 7/1981 | KIerkhoffs | 435/99 |
| 4,734,402 | 3/1988 | Hashimoto et al. | 514/54 |
| 4,788,065 | 11/1988 | Nakamura et al. | 426/2 |
| 5,502,273 | 3/1996 | Bright et al. | 800/205 |

FOREIGN PATENT DOCUMENTS

| | | | |
|---|---|---|---|
| WO89/12386 | 12/1989 | WIPO | A01H 1/04 |
| WO90/11361 | 10/1990 | WIPO | C12N 15/82 |
| WO92/11375 | 7/1992 | WIPO | C12N 15/56 |
| WO92/14827 | 9/1992 | WIPO | C12N 15/82 |
| WO94/04692 | 3/1994 | WIPO | C12N 15/82 |
| WO 94/14970 | 7/1994 | WIPO . | |

OTHER PUBLICATIONS

Stam M, et al. "The silence of genes in transgenic plants." Ann. Bot. 79: 3–12, 1997.
Koziel MG, et al. "Optimizing expression of transgenes with an emphasis on post–transcriptional events." Plant Mol. Biol. 32: 393–405, 1996.
Smith CJS, et al. "Antisense RNA inhibition of polygalacturonase gene expression in transgenic tomatoes." Nature 334: 724–726, Aug. 25, 1988.
van der Meer IM, et al. "Fructan as a new carbohydrate sink in transgenic potato plants." Plant Cell 6: 561–570, Apr. 1994.
Burne RA, et al. "Cloning and expression of a Streptococcus mutans glucosyltransferase gene in *Bacillus subtilis*." Gene 47: 201–209, 1986.
Twell D, et al. "The 5' flanking DNA of a patatin gene directs tuber specific expression of a chimearic gene in potato." Plant Mol. Biol. 9: 345–375, 1987.
de Pater S, et al. "A 22 bp fragment of the pea lectin promoter containing essential TGAC–like motifs confers seed–specific gene expression." Plant Cell 5: 877–886, Aug. 1993.
Salunkhe and Desai, *Postharvest Technol. of Sugar Crops*, CRC Press, Boca Raton, FL, pp. 16–27, 1988.
Stout, *J. Am. Soc. Sugar Beet Technol.*, 9, 350, 1957.
Barnes, *The Sugarcane*, 2nd ed., Leonard Hill Books, London, pp. 358–394, 1974.
Alexander, *Sugarcane Physiology*, Elsevier, Amsterdam, 573–609, 1973.
Gulibeau, et al, *Sugar J.*, 18, 30, 1955.
Finker, et al., *J. Am. Soc. Sugar Beet Technol.*, 10, 459–466, 1959.
Brown, *Anal. Chem.*, 24(2), 384–388, 1952.
Hendry, *New Phytol.*, 106, 201–216, 1987.
Nelson and Spollen, *Physiol. Plant*, 71, 512–516, 198.
Fuchs, *Starch*, 39, 335–343, 1987.
Haunold, et al., *J. Plant Physiol*, 134, 218–223, 1989.
Dykins, et al., *Industrial Engineering and Chemistry*, 25, 937–940, 1933.
Praznik and Beck, *Agr. Biol. Chem.*, 51(6), 1593–1599, 1987.
Eddelman and Jefford, *New Phytol.*, 67, 517–531, 1968.
Wagner, et al., *Zeitschrigt fur Pflanzenphysiologie*, 112, 359–372, 1983.
Frehner, et al., *New Phytol.*, 116, 197–208, 1984.
Housley, et al., *New Phytol*, 119, 491–497, 1991.
Cairns, A. J., *New Phytol.*, 120, 463–473, 1992.
Hehre, *Adv. in Enzymol.*, 11, 297–337, 1951.
Hestrin, *The Bacteria: A Treatise on Structure and Function*, Academic Press, NY, Gunsalas and Stanier eds., 3, chap. 8, 1962.
Hestrin, *Ann. N.Y. Acad. Sci.*, 66, 401–409, 1956.
Hehre, *Methods Enzymol.*, 1, 178–192, 1955.
Han, *Adv. Appl. Microbiol*, 35, 171–194, 1990.

(List continued on next page.)

*Primary Examiner*—Douglas W. Robinson
*Assistant Examiner*—Amy J. Nelson

[57] ABSTRACT

This invention concerns methods for synthesis and accumulation of fructose polymers in seed, tubers or leaves of transgenic plants by selective expression of a bacterial fructosyltransferase gene. Selective expression includes coordination of timing, tissue specific expression and especially subcellular location. Successful transformants utilize sucrose to synthesize and accumulate fructan in the vacuole of the cell, in established crops, without loss of co-products or concern for yield loss due to degradation during maturation, harvest or storage of the plant. Enhanced fructan production will benefit the fructose sweetener industry and add value to grain used for feed.

11 Claims, No Drawings

OTHER PUBLICATIONS

Evans and Hibbert, *Adv. Carbohydr. Chem.*, 2, 253–277, 1946.

Mantsala and Puntala, *FEMS Microbio. Lett.*, 13, 395–399, 1982.

Kleczowski and Wierzchowski, *Soil Sci.*, 49, 193–195, 1940.

Chambert, et al., *Eur. J. Biochem*, 41, 285–300, 1974.

Berthou, et al., *J. Mol. Biol.*, 82, 111–113, 1974.

Fouet, et al., *Biochem. Biophys. Res. Commun.*, 119(2), 795–800, 1984.

Shiroza, T., et al., *J. Bacteriol.*, 170(2), 810–816, 1988.

Tang, et al., *Gene*, 96, 89–93, 1990.

Chambert, et al., *Biochem J.*, 279, 35–41, 1991.

Visser, et al., *Plant Mol. Biol*, 17, 691–699, 1991.

Wentzler, et al., *Plant Mol. Biol.*, 12, 41–50, 1989.

Stitt, et al., *Planta*, 183, 40–50, 1990.

Krapp, et al., *The Plant J.*, 3(6), 817–828, 1993.

Schiweck, et al., *Carbohydrates as Organic Raw Materials*, Lichtenthaler ed., VCH Press, NY, 72–82, 1992.

Farnworth, et al., *Inulin and Inulin Containing Crops*, Fuchs ed. Elsvier, Amsterdam, 385–389, 1993.

Cote, *Carbo. Polym.*, 19, 249–252, 1992.

Giffard, et al., *J. Gen. Micro.*, 139, 1511–1522, 1993.

Hidaka and Hirayama, *Biochem. Soc. Trans.*, 19, 561–565, 1991.

Fuchs, *Biochem. Soc. Trans.*, 19, 555–560, 1991.

van der Meer, I.M. et al, *The Plant Cell*, 6, 561–570, Apr. 1994.

Chatterton et al., Plant Cell Physiol, 29(7), 1103–1108, 1988.

ACCUMULATION OF FRUCTANS IN PLANTS BY TARGETED EXPRESSION OF BACTERIAL LEVANSUCRASE

CROSS-REFERENCE TO RELATED APPLICATIONS

This is the national stage of international application PCT/US94/12778, filed Nov. 7, 1994, which is a continuation-in-part of U.S. patent application Ser. No. 08/149,689, filed Nov. 9, 1993 now abandoned.

FIELD OF THE INVENTION

This invention concerns methods for synthesis and accumulation of fructose polymers in transgenic plants by selective expression of bacterial fructosyltransferase genes.

TECHNICAL BACKGROUND

The major reserve carbohydrates found in vascular plants are sucrose, starch and fructan, (a non-reducing polymer of fructose linked to a terminal glucose residue). Despite numerous agronomic and technical barriers, crops are grown throughout the world specifically as sources of sucrose or starch for use primarily, in the sweetener industry.

Economically successful cultivation and processing of sugar beet and sugarcane for sucrose must overcome obstacles including, but not limited to, restricted growing regions, labor intensive harvesting practices, critical timing of harvest when sucrose levels reach their peak, undesirable changes in composition and quality brought on by delay in transport or processing, and yield loss due to improper or long term storage (Salunkhe and Desai, Postharvest Technol. of Sugar Crops, CRC Press, Boca Raton, Fla. (1988); Stout, J. Am. Soc. Sugar Beet Technol., 9:350 (1957); Barnes, The Sugarcane, 2nd. ed., Leonard Hill Books, London (1974)). Processing of sugarcane for example, only 9 days after it has been cut is an unprofitable exercise due to the tremendous loss of sucrose by enzymatic degradation, (Alexander, Sugarcane Physiology, Elsvier, Amsterdam, (1973); Gulibeau et al., Sugar J., 18:30 (1955)). Because of the relatively short period of profitability, the timing of harvest and processing requires rigorous planning. Unexpected delays, such as those for extreme weather conditions, may result in significant loss of product. Optimum harvest periods for sugar beet are also complicated by issues of timing. Raffinose, the primary contaminant of beet juice, inhibits the crystallization of sucrose and presents a considerable challenge to profitable sugar beet processing. Raffinose has been shown to increase dramatically during the same period when sucrose levels peak and continues to increase during storage of beets at temperatures needed to prevent sucrose degradation (Finkler et al., J. Am. Soc. Sugar Beet Technol., 10:459 (1959); Brown, Anal. Chem., 24:384 (1952)). Cultivation of sugar beet for sucrose is complicated then, because the level of sucrose and amount of raffinose determine the quality and therefore the profitability of sugar beet processing.

Starch based sweeteners, produced mostly from corn, were developed in part because of the many limitations associated with sugarcane and sugar beets. Corn sweeteners also helped to relieve dependence on importation of sucrose. Supply had historically, been subject to world shortages and volatile price swings, brought about through a number of political events and natural diastase.

The shift away from sucrose crops in the United States was remarkably rapid, possibly due to the many advantages inherent in producing sweeteners from starch. One, for example is that harvest and storage conditions for corn are much more favorable compared to sucrose crops such as sugar beet and sugarcane. This allows much longer storage time, without quality loss while waiting for available process capacity. Profitable production of sucrose from sugarcane must take place within a few days of harvest to prevent quality losses. In contrast, corn may be held in proper storage for a year before isolation of starch for sweetener production, without significant loss or alteration of product. Another advantage corn has over crops such as sugarcane, is the adaptation to a greater variety of growing conditions. The use of corn vastly increased the amount of acres in the United States available to growing a crop for the sweetener industry. Furthermore, fructose, the end product of starch based sweeteners, is preferred over sucrose by major consumers due to its enhanced relative sweetness. Under acidic conditions, fructose may be up to 1.8 times sweeter than sucrose. This results in a savings to the consumer because less product may be used to produce the same effect.

Despite the commercial success of the fructose corn syrup industry, there is considerable room for improvement. Technical hurdles that must be overcome to convert starch, a glucose polymer, into fructose add significantly to the cost of production. The current technology of fructose syrup production essentially begins with the hydrolysis of starch into individual glucose residues. This is accomplished by enzymatic hydrolysis, in order to reduce off colors, flavors and poor yield due to unusable oligomers formed when hydrolysis of starch is accomplished through a mild acid treatment. Enzymatic hydrolysis of starch, efficient though it may be, results in significant monetary loss because of the massive scale of fructose syrup production. A 96% conversion of starch to glucose results in a tremendous loss in potential product, considering the several hundred million pounds of starch hydrolyzed each year. With as little as 4% loss, due to incomplete hydrolysis of starch, the result may be a loss amounting to tens of millions of pounds of potential glucose that would otherwise be sold as the final product. The effect is a loss of millions of dollars of potential revenue each year.

The efficiency of the total process is reduced even further during the isomerization step. Conversion of glucose to fructose, enzymatically, reaches equilibrium at only 42% fructose. This mixture of fructose and glucose is not an acceptable product. The industry standard is sucrose and the 42% fructose solution is not comparable in terms of sweetness to an equivalent sucrose solution. The consequence is that the 42% solution must be enriched for fructose by ion exchange chromatography which adds significantly to the total cost of production. A 90% fructose solution is eluted from the ion exchange column and blended with a portion of the 42% fructose solution to obtain a 55% product. The 55% fructose solution has an equivalent level of sweetness compared to sucrose.

The fastest growing market for fructose sweeteners today is for crystalline fructose. This product is used in a growing number of baked goods and dry mixes. Production of crystalline fructose requires that the 90% fructose syrup isolated from ion exchange columns undergo additional processing, which adds to its cost. Additional processing is necessary to further remove glucose contamination before crystallization of fructose is possible. A mixture of approximately 97% fructose is needed to obtain this product which sells for a premium.

Conversion of a glucose polymer (starch), into fructose has a number of advantages in the sweetener industry, but they come at significant cost. The issue of cost could be addressed by substituting fructan as the starting material for fructose syrup production. The third member of plant carbohydrate storage reserves fructans, have been known for over 150 years. Fructans consist of individual fructose residues connected by β2-1 and β2-6 linkages. Simple hydrolysis, of this polymer by either enzymatic or mild acid treatment yields substantially pure fructose. Fructans, therefore, offer a unique advantage over starch in purity and content that would result in the elimination of saccharification, isomerization, and ion exchange steps, currently utilized in fructose syrup production. Simplified processing, resulting in a reduction of costs and the higher relative sweetness of fructose compared to sucrose are only two reasons why fructans are considered to be excellent starting materials for the sweetener industry.

The disadvantages of cultivating fructan containing crops however, are comparable to those grown for sucrose. Although 23 separate plant families have been shown to accumulate fructans (Hendry, New Phytol., 106:201–216 (1987); Nelson and Spollen, Physiol. Plant, 71:512–516 (1987)), only two species are considered as potential industrial crops. Jerusalem artichoke (*Helianthus tuberosus*) and Chicory (*Cichorium intybus*), are known to be as productive as traditional agricultural crops, accumulating carbohydrate levels, comparable to sugar beet and potato (Fuchs, Starch 39:335–43 (1987)). Jerusalem artichoke and chicory are however, seasonable crops. Fructans are stored in below ground tubers during only a portion of the growing season. Fructan synthesis falls off rapidly after tuber development ceases. Degradation activity increases in the tuber during maturation and remains high during the dormant period (Fuchs, Starch 39:335–43 (1987)). Timing of harvest is particularly critical for Jerusalem artichoke. The desirable larger molecular weight polymers are more prevalent in young tubers when relatively little of the potential amount of fructan has accumulated. The mature tubers contain up to 80% of their dry weight as fructan, but the predominant species are of the lower molecular weight type, (Haunold et al., J. Plant Physiol. 134:218–223 (1989)). Because all fructans contain a terminal glucose residue, originating from the starting sucrose molecule, the larger the number of fructose residues the more pure the polymer. Less purification of fructose from glucose contamination is needed then, with the larger fructans. Intensive processing of fructans during a short, but critical time of the year may circumvent losses due to degradation, but this would be subject to processing capacity. Processing capacity would in turn, certainly be limited by the costs needed to build specialized equipment and commercial plants capable of processing a unique root crop, during the short harvest season.

A major disadvantage of cultivating Jerusalem artichoke for commercial harvest of fructan is the thin delicate skin of the tuber. Injury to the tuber often occurs during harvest, increasing respiration, which results in high water loss and increased fructan degradation during storage. Storage under ambient conditions is limited to only a few weeks, at best before significant degradation of fructans reduces economic success. Alternatively, the crop could be maintained in storage at a constant temperature and humidity until processed. This would prevent product loss (Dykins et al., Industrial and Engineering Chemistry, 25:937–940 (1933)) however, the expense involved for large scale storage is prohibitive.

Fructan accumulation in the field is extremely sensitive to environmental change. Exposure to drought or frost dramatically alters the quality of the fructan accumulated (Praznik and Beck, Agr. Biol. Chem., 51:1593–1599 (1987)). Traditional breeding programs could in theory, result in varieties with reduced quality losses due to environmental change. However, programs of this type, normally very time consuming, are not in place at this time and would likely be implemented only when the fructan industry proves to be viable. Genetic engineering of fructan containing crops could also eliminate these barriers. Overexpression of a fructan biosynthetic gene or genes, may lead to increased yield, synthesis of larger molecular weight fructans or reduced quality losses due to frost or drought. This approach could also potentially eliminate the need for specialized storage conditions. Success of such a genetic program would rely heavily on a detailed understanding of the biochemistry of fructan synthesis, the kinetics of the biosynthetic proteins and ultimately, understanding the regulation of the genes involved in fructan synthesis. At present, this knowledge is lacking. The current model for all fructan accumulating plants, proposed in 1968 (Eddleman and Jefford, New Phytol. 67:517–531 (1968)), suggests that polymer synthesis and storage is achieved by the sequential action of two separate proteins. The model, which has been slightly altered, (Wagner et al., Zeitschrigt fur Pflanzenphysiologie 112:359–372, (1983); Frehner et al. 1984, New Phytol. 116:197–208) has yet to resolve a key issue regarding reversible fructosyltransferase (FTF) activity and is once again under critical review (Housley et al., New Phytol. 119:491–97, (1991); Cairns, A. J., New Phytol. 120:463–73 (1992)). Enzymes involved in the biosynthesis pathway have not been purified to homogeneity. Therefore, attempts to fully understand fructan metabolism and then to alter regulation of synthesis, control loss due to degradation and increase the molecular weight of accumulated fructans in a transgenic plant using a cloned plant gene or genes may be several years away.

Microorganisms are also known to produce fructans. However, unlike plant systems, microbial fructan synthesis is well characterized (reviewed in: Hehre, Adv. in Enzymol., 11:297 (1951); Hestrin, The Bacteria: A Treatise on Structure and Function, Academic Press, NY, Gunsalas and Stanier eds., Vol. 3, chap. 8 (1962)) FTFs derived from bacterial sources catalyze the polymerization of linear or branched polymers containing β2-1, β2-6 or combinations of β2-1 and β2-6 linked fructose residues. Chains of fructan, similar to starch and dextran, grow by a step-by-step addition of a single fructofuranosyl residue at the C-6 hydroxyl of the nonreducing fructose terminal unit in the growing chain. Alternatively, branches in the chain occur when the addition of fructose residues occurs at the C-1 hydroxyl. Branching may occur at a rate of up to 12% of the polymer (Hestrin, Ann. N.Y. Acad. Sci., 66:401 (1956); Hehre, Methods Enzymol. 1:178–192 (1955); Han, Adv. Appl. Microbiol. 35:171–194 (1990)). Most extensively studied in *Bacillus subtilis,* many species have been identified that posses fructose polymerizing activity (Evans and Hibbert, Adv. Carbohydr. Chem., 2:253–277 (1946); Mantsala and Puntala, FEMS Microbio. Lett., 13:395–399 (1982); Kleczowski and Wierzchowski, Soil Sci., 49:193 (1940)). Bacterial proteins have been purified to homogeneity (Chambert et al. Eur. J. Biochem. 41:285–300 (1974)) and crystallized (Berthou et al., J. Mol. Biol., 82:111–13 (1974)). Exhaustive study of the purified bacterial FTF activity led to the finding that polymers are synthesized by a single protein acting on sucrose, the sole substrate. The fructose chain grows by the repeated transfer of fructose from a donor sucrose to an acceptor fructan polymer. Synthesis has been demonstrated to be independent of the need for cofactors or primers.

Purified protein allowed identification and cloning of the bacterial FTF gene from several species (Fouet, A., Arnaud, M., Klier, A. and Rapoport, G., Biochem. Biophys. Res. Commun. 119, 795–800 (1984); Shiroza, T. and Kuramitsu, H. K., J. Bacteriol. 170, 810–816 (1988); Tang, L. B., Lenstra, R., Borchert, T. V. and Nagarajan, V. Gene 96, 89–93 (1990)). The cloned genes and site directed mutagenesis provided additional information concerning binding regions, kinetics and intermediate protein-sugar complexes (Chambert, R., and Petit-Glatron, M. F., Biochem. J., 279, 35–41 (1991)).

Microbial fructan biosynthesis is well understood allowing regulation of plant fructan accumulation through genetic engineering. The cloned bacterial genes present opportunities to alter fructan containing crop species, or to accumulate fructans in transgenic agricultural crops where they are not normally found in nature. However, with sucrose as the sole substrate, many potential barriers to successful expression in a transgenic plant must be considered. Expression of a bacterial gene with sucrose metabolic properties in a transgenic plant must be in consideration of the critical role sucrose plays in the growth and development of higher plants. Most compounds formed in nonphotosynthetic tissues of a plant are derived from sucrose. Sucrose concentration has been shown to regulate gene expression (Visser et al., Plant Mol. Biol., 17:691–699 (1991); Wentzler et al., Plant Mol. Biol., 12:41–50 (1989)) and has a demonstrated role in regulating the rate of photosynthesis, (Stitt et al., Planta, 183:40–50 (1990); Krapp et al., The Plant J., 3:817–828 (1993)). These roles cannot, and should be ignored. Indiscriminate expression of a gene with the capacity to alter sucrose concentration in a transgenic plant may deprive nonphotosynthetic tissue of a crucial metabolite where it is most needed and could have serious consequences on the development of that tissue. Altered concentration would also alter gene expression, linked to sucrose level in the cell, leading to unknown, but certainly serious negative results.

Specialized structures in higher plants exist to transfer, collect and concentrate sucrose. Sucrose levels therefore, are considerably varied throughout a plant, within cellular organelles and among species. Although sucrose is the dominant form of carbohydrate transported from net carbon exporting tissue (source) to net carbon importing tissue (sink), many plants transport alternate forms of sucrose (e.g., raffinose) or alternate carbohydrates altogether (e.g., mannitol or sorbitol). Successful expression of a sucrose metabolizing enzyme across a varied population of plant species, without altering regulatory signals and subcellular expression sequences is then, highly unlikely. Expression must only be in consideration of the multiple mechanisms that exist to transport and concentrate sucrose, altered forms of sucrose that exist in higher plants and the critical role sucrose plays in various plant tissues.

Accumulation of bacterial fructans in transgenic plants offers several advantages over plant fructans. Fructan size is the most notable difference between fructans from plant and microbial sources. Plant polymers are low molecular weight with an average of 10–30 fructose units per molecule. In contrast, microbial fructans may contain over 100,000 fructose residues with a molecular weight of up to $10^6$–$10^8$. Increased fructan size, in the context of this invention, is a great advantage because the larger the polymer, the greater the fructose to glucose ratio and the less purification necessary to remove contaminating glucose following hydrolysis. Increased size is also an advantage because the larger bacterial fructans are much less water soluble than are the smaller plant polymers. The difference in solubility may be taken advantage of when processing tissue. Separating fructans from highly soluble cell material such as sucrose, glucose and other sugars, would be less technically difficult if the polymers to be isolated, were of the larger size. The large fructans also offer the opportunity to store more fructose in a cell without altering internal osmotic pressure compared to the same amount of fructose in smaller polymers. Since altering osmotic pressure in a sink tissue is critical to import of carbon, this advantage may be most significant of all.

Fructan accumulation in a transgenic plant may be an attractive alternative to the current fructose sweetener technology. Especially true in corn, a fructose polymer will not alter the advantages gained over sucrose crops, but instead, builds on them. Fructan production in corn for example, allows the utilization of the corn by-products (oil, meal and gluten feed) in addition to removing the tremendous costs of converting glucose to fructose. Hydrolysis of fructan into individual fructose residues results in a product consisting of at least 99% fructose. This highly pure product provides an alternative to the inefficient isomerization step and eliminates the need for fructose enrichment by ion exchange chromatography. Crystallization of fructose is simplified by starting with material that consists of 99%(+) fructose.

Reducing the cost of production is significant not only to the sweetener industry, but the use of fructose as a chemical feedstock is dependent on availability, purity and competitive price. At present the fructose industry can meet only the demands of purity. The United States is the largest producer of fructose syrups but, is a net importer of fructose. Food uses currently consume more fructose than is produced. Availability at a competitive cost would allow fructose, easily dehydrated to 5-hydroxymethyl-furfural (HMF) to be utilized as a building block for pharmaceuticals, such as Ranitidine or Zantac™, currently the best selling antiulcer drug. HMF may also be used as starting material for polymers, such as Kevlar™, and Nomex™, in addition to the potential for use in opto-electronic devices, due to the special optical effects of the furan nucleus (Schiweck et al., in Carbohydrates as Organic Raw Materials, Lichtenthaler ed., VCH Press, NY, pp. 72–82, (1992)). HMF may be converted into carbocyclic and heterocyclic compounds, creating a role in almost every part of applied chemistry, if only its purity could be combined with increased production and reduced cost.

The addition of very low levels of fructans in feed preparations was recently shown to bring about several positive metabolic and physiological changes in monogastric animals (Hashimoto et al., U.S. Pat. No. 4,734,402 (1988); Nakamura et al., U.S. Pat. No. 4,788,065 (1988); Farnworth et al., Inulin and Inulin Containing Crops, Fuchs ed., Elsvier, Amsterdam, pp 385–389 (1993)). The probiotic effect of fructans in feed may be attributed to an increase in the population of beneficial microflora in the intestine. Reduced instances of scours and increased feed efficiency has obvious potential benefit for domestic animal production. Accumulation of fructan within the grain is an advantage not only for the value as a probiotic, but allows "on farm" use without the need for expensive equipment needed in grinding or blending feeds.

Transformation of plants with a FTF results in the introduction of a gene that would not otherwise be possible through traditional breeding, but would take advantage of inbred or elite lines, well adapted to specific growing regions. Transforming with a bacterial FTF gene will result in a renewable source of a valuable polymer without the loss of established co-products such as oil, gluten feed and meal, in the case of corn. Transgenics also offer the advantage of accumulation of a fructan in a plant that does not have the capability of degrading that polymer. This means that environmental changes will not alter quality or quantity of the polymer as seen in plants such as Jerusalem artichoke and chicory. The transgenic tissue could be stored with less concern for degradation. Long term storage in unspecialized containers will reduce or eliminate the costs and technical needs associated with harvest and isolation from current fructan crops.

Methods described in this invention would enable commercial scale production of fructose polymers, as well as polymers of glucose. FTFs belong to a group of similar proteins known as sucrases which posses the ability to polymerize carbohydrate, using sucrose as the sole substrate. The sucrase family of proteins are similar in many respects for example, the proteins are catalytically active as monomers and no cofactors or primers are required for synthesis. The family of proteins would be expected to function as does the chimeric FTF in transgenic plants, based on the remarkable similarities within the group. The final product may contain polymerized fructose as is catalyzed by FTFs, but glucose may also be polymerized by sucrases known as glucosyltransferases (GTFs). GTFs vary in source as well as in function, and the type of polymer catalyzed varies accordingly. A number of GTFs (i.e., alternansucrase, GTF-I, GTF-S and GTF-SI, (Cote, Carbo. Polym., 19:249–252 (1992); Giffard et al., J. Gen. Micro., 139:1511–1522 (1993)) have been identified and each catalyzes the formation of a slightly different polymer. The polymer may vary in size, in linkage type or in pattern of linkages. As is true with starch, also a glucose polymer, the difference in size, linkage type and pattern of linkages determines the properties, which influences its commercial use. GTFs, such as certain dextransucrases, may polymerize glucose through unique linkages, resulting in properties very different from those of starch. GTFs are currently used to produce a glucose polymer, dextran for high value uses in research and as a volume extender of blood plasma. Large scale production of these alternate polymers offers options very much like those described for fructans, including providing a renewable source of unique polymers, reducing the production cost of polymers with demonstrated markets and opening markets through uses that would not otherwise be cost-effective.

WO89/12386 describes a method for the production of glucose and fructose polymers in transgenic tomato plants. The disclosure in that patent application describes exposure in the cytosol which may not be enabling, and further, results in destruction of transformed cells. WO89/12386 does not teach insertion in the vacuole.

The present invention details a method and the materials necessary for the synthesis and accumulation of fructose polymers in a transgenic plant where the polymer does not normally exist and in plant species without the ability to hydrolyze or alter the qualities of the polymer once accumulated. Accumulation of fructose polymers in transgenic plants has been accomplished through the tissue specific and sub-cellular expression of a bacterial fructosyltransferase (FTF) gene, using sucrose as a sole substrate and requiring no cofactors or externally supplied primers. Particular attention is paid to the level of sucrose in a particular cell, the timing of FTF expression, tissue specific expression in plant species and to subcellular location of expression. These issues, critical to the success of the invention, were not described or considered in previous publications.

This present invention describes a unique combination of tissue specific promoters, a vacuole targeting sequence, a coding sequence for a microbial FTF and a method for transferring the DNA fragments into tobacco, potato and corn. The result is a method for the production and accumulation of fructose polymers which would also be applicable to other polymers synthesized by proteins within the sucrase family of enzymes. The methods described may be used in alternate agronomic crops that accumulate significant quantities of sucrose, such as sugar beet and sugarcane. In addition fructan containing crops, such as chicory or Jerusalem artichoke may be improved by the methods described in the present invention. The effect of this technology is a method of large scale production of unique polymers, especially fructans, at reduced cost which have use as sweeteners, a polymer with beneficial properties for human-health (Hidaka and Hirayama, Biochem. Soc. Trans., 19:561–565 (1991)), probiotics in the animal feed industry (Hashimoto et al., U.S. Pat. No. 4,734,402 (1988); Nakamura et al., U.S. Pat. No. 4,788,065 (1988)), and may be used as chemical feedstock in new markets that would not otherwise be economically successful (Fuchs, Starke, 39:335–342, (1981); Fuchs, Biochem. Soc. Trans., 19:555–560, (1991)). Accumulation of fructans has been demonstrated not to be harmful to the growth, development or reproductive capacity of the transgenic plants.

SUMMARY OF THE INVENTION

This invention concerns a recombinant DNA construct comprising a tissue specific promoter, operably linked to a vacuole targeting sequence, operably linked to a coding sequence for a levansucrase gene such that said construct is capable of transforming a plant cell selected from the group consisting of corn, potato, and tobacco to obtain production of fructan in the vacuole of said plant cell without deleterious effect on said plant cell. The invention also concerns a plant selected from the group consisting of corn, potato, and tobacco transformed with said construct, such that said plant produces fructan which accumulates in the vacuole of the cells of the plant. The invention further concerns s method of producing fructose comprising growing the said described plant, harvesting said plant, and extracting said fructan from the harvested plant.

The invention further concerns a recombinant DNA construct comprising a tissue specific promoter, operably linked to a vacuole targeting sequence, operably linked to a coding sequence for a dextran-sucrase gene such that said construct is capable of transforming a plant cell selected from the group consisting of corn, potato, and tobacco to obtain production of dextran in the vacuole of said plant cell without deleterious effect on said plant cell. The invention also concerns a plant selected from the group consisting of corn, potato and tobacco transformed with said construct, such that the plant produces dextran which accumulates in the vacuole of the cells of the plant. The invention further concerns a method of producing dextran comprising growing the plant described, harvesting said plant, and extracting said dextran from the harvested plant.

The invention additionally concerns a recombinant DNA construct comprising a tissue specific promoter, operably linked to a vacuole targeting sequence, operably linked to a coding sequence for an alternansucrase gene such that said construct is capable of transforming a plant cell selected from the group consisting of corn, potato, and tobacco to obtain production of alternan in the vacuole of said plant cell without deleterious effect on said plant cell. The invention also concerns a plant selected from the group consisting of corn, potato and tobacco transformed with said construct, such that the plant produces alternan which accumulates in the vacuole of the cells of the plant. The invention also concerns a method of producing alternan comprising growing said plant, harvesting said plant, and extracting said alternan from the harvested plant.

DEFINITIONS

In the context of this disclosure, a number of terms shall be utilized. As used herein, the terms "promoter" and "promoter region" refer to a sequence of DNA, usually upstream (5') to the coding sequence of a structural gene, which controls the expression of the coding region by providing the recognition for RNA polymerase and/or other factors required for transcription to start at the correct site. Promoter sequences are necessary, but not always sufficient to drive the expression of the gene. A "promoter fragment" constitutes a fraction of the DNA sequence of the promoter region. A "3' downstream region" (or "3' end") refers to that portion of a gene comprising a DNA segment, excluding the 5' sequence which drives the initiation of transcription and the structural portion of the gene, that contains a polyadenylation signal and any other regulatory signals capable of affecting messenger RNA (mRNA) processing or gene expression. The polyadenylation signal is usually characterized by affecting the addition of polyadenylic acid tracts to the 3' end if the mRNA precursor. Polyadenylation signals are commonly recognized by the presence of homology to the canonical form 5'-AATAA-3', although variations are not uncommon.

"Nucleic acid" refers to a large molecule which can be single or double stranded, composed of monomers (nucleotides) containing a sugar, phosphate and either a purine or pyrimidine. In higher plants, deoxyribonucleic acid (DNA) is the genetic material while ribonucleic acid (RNA) is involved in the translation of the information from DNA into proteins. The term "nucleotide sequence" refers to a polymer of DNA or RNA which can be single- or double stranded, optionally containing synthetic, non-natural or altered nucleotide bases capable of incorporation into DNA or RNA polymers.

"RNA transcript" refers to the product resulting from the RNA polymerase catalyzed transcription of a DNA sequence. The RNA transcript may be a perfect complimentary copy of the DNA sequence and is referred to as the primary transcript or it may be an RNA sequence derived from posttranscritptional processing of the primary transcript and is referred to as the mature RNA.

As used herein, "Gene" refers to a DNA sequence that codes for a specific protein. "Native" gene refers to the gene as found in nature. "Chimeric" gene refers to a gene comprising heterologous regulatory and/or coding sequences. "Mutant" gene refers to a gene with alterations in the nucleotide sequence, different than that ordinarily found in nature. They may be intentional or accidental and result in altered activity, but may not necessarily alter the gene product.

As used herein, "suitable" or "appropriate" regulatory sequence refers to a nucleotide sequence located upstream (5'), within, and/or downstream (3') to a DNA sequence for a selected gene product whose transcription and expression is controlled by the regulatory sequence, potentially in conjunction with the protein biosynthetic apparatus of the cell. "Regulation" or "regulate" refer to the modulation of the gene expression induced by DNA sequence elements located primarily, but not exclusively upstream of (5') the transcription start of the gene. Regulation may result in an all or none response to a stimulation, or it may result in variations in the level of gene expression. "Constitutive expression" refers to continuous expression, regardless of change in stimulus other than that necessary to regulate itself.

"Responsive" or "response", as used herein, refer to the change in the expression level of a regulated promoter or gene following the application of an environmental stimulus.

The term "coding sequence" refers to that portion of a gene encoding a protein, polypeptide, or a portion thereof, and excluding the regulatory sequences which drive the initiation of transcription. The coding sequence may be one normally found in the cell or it may be one not normally found in a cellular location, in which case it is termed a "heterologous gene". A heterologous gene may be derived in whole or in part from any source known to the art, including a bacterial genome or episome, eukaryotic nuclear or plasmid DNA, cDNA, or chemically synthesized DNA. The structural gene may constitute an uninterrupted coding region or it may include one or more introns bounded by appropriate splice junctions. The structural gene may be a composite of segments derived from different sources, naturally occurring or synthetic.

The term "recombinant DNA construct" or simply "construct" refers to a plasmid, virus, or autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with an appropriate 3' untranslated sequence into a plant cell.

As used herein, "plant" refers to whole plants and plant-derived tissues. "Plant derived tissues" refers to differentiated and undifferentiated tissues of a plants, including, but not limited to roots, shoots, leaves, pollen, ovules, tubers, seeds and various forms of cells in culture such as intact cells, protoplasts, embryos and callus tissue. Plant-derived tissues may be in planta, or in organ, tissue or cell culture. A "monocotyledonous plant" refers to a plant whose seeds have only one cotyledon, or organ of the embryo that stores and absorbs food. A "dicotyledonous plant" refers to a plant whose seeds have two cotyledons. As used herein, "transformation" refers to the processes by which cells, tissues or plants acquire properties encoded on a nucleic acid molecule that has been transferred to the cell, tissue or plant. "Transferring" refers to methods to transfer DNA into cells including, but not limited to microinjection, permeabilizing the cell membrane with various physical (e.g., electroporation) or chemical (e.g., polyethylene glycol, PEG) treatments.

The term "operably linked" refers to the chemical fusion of two or more fragments of DNA in a proper orientation such that the fusion preserves or creates a proper reading frame, or makes possible the proper regulation of expression of the DNA sequences when transformed into plant tissue.

The term "expression" as used herein is intended to mean the transcription and/or translation to gene product from a gene coding for the sequence of the gene product. In the expression, a DNA chain coding for the sequence of a gene product is first transcribed to a complementary RNA which is often a mRNA and then, the thus transcribed mRNA is translated into the above-mentioned gene product if the gene product is a protein. Expression, which is constitutive and further enhanced by an externally controlled promoter fragment thereby producing multiple copies of mRNA and large quantities of the selected gene product, is referred to as "over-production". "Expression cassette" is used to refer to a DNA construct containing a promoter region operably linked to a coding sequence, which is operably linked to a 3' end and together is capable of directing a mRNA of the coding region, resulting in synthesis of the protein product in plant tissue.

The "translation start codon" or "initiation codon" refers to a unit of three nucleotides (codon) in a nucleic acid sequence that specifies the initiation of protein synthesis.

The term "signal peptide" refers to the N-terminal extension of a polypeptide, which is translated in conjunction with the polypeptide forming a precursor protein and which is required for its entrance into the secretory pathway. The signal peptide may be recognized by the mechanisms within the same species or unrelated species plants, necessary for direction of the peptide into the secretory pathway. The signal peptide may be active in seeds, leaves, tubers and other tissues of the plant. The term "signal sequence" refers to a nucleotide sequence that encodes a signal peptide. The term "vacuole targeting signal" refers to the N-terminal extension of a polypeptide, which is translated in conjunction with the polypeptide forming a precursor protein and which is required for its eventual entrance into the vacuole of a cell. The vacuole targeting signal may be recognized by the mechanisms within the same species or unrelated species plants, necessary for direction of the peptide into the vacuole of a cell. Vacuole targeting signals may be active in seeds, leaves, tubers and other tissues of the plant. The term "vacuole targeting sequence" refers to a nucleotide sequence that encodes the vacuole targeting signal. A "vacuole" is considered to be a membrane bounded compartment of a plant cell that may vary in size, function, and content. The vacuole may contain cell metabolites and the number of vacuoles within a cell may vary greatly from one cell to another or from the cells in one tissue type to the next.

A "tissue specific promoter" refers to a sequence of DNA which provides recognition signals for RNA polymerase and/or other factors required for transcription to start, controlling expression of the coding sequence precisely within certain tissues or within certain cells of that tissue. Expression in a tissue specific manner may be only in individual tissues or cells within tissues or in combinations of tissues. Examples may include, but are not limited to tissue specific expression in leaves only and no other tissue within the plant, or may be in petals, ovules and stamen and no other tissues of the plant.

"Heritable" refers to the ability of a plant to develop to maturity, sexually or asexually, producing seed or by other means is capable of delivering its genetic content, in full or part, to progeny. The genetic content of the progeny is responsible for growth and development of the new plant with properties or traits, similar or identical to the parent plant.

"Levansucrase" refers to a protein coded for by any one of several organisms which has the property of synthesizing a carbohydrate polymer consisting of repeating fructose residues, using sucrose as a substrate. The repeating fructose residues may be linked by β2-1 linkage or a β2-6 linkage or any combination of the two linkage types. This protein may also be known as a "fructosyltransferase" (FTF) or a protein which has FTF activity. The polymer of repeating fructose residues may contains one terminal glucose residue, derived from a sucrose molecule, and at least two fructose residues. The polymer of repeating fructose residues in any form, with any combination of linkages, and with any number of fructose residues, is referred to generally as a "fructan". A "levansucrase gene" refers to the DNA sequence coding for a levansucrase protein.

"Dextransucrase" refers to a protein coded for by any one of several organisms which has the property of catalyzing the polymerization of a carbohydrate polymer consisting of repeating glucose residues linked exclusively by either α1-6 or α1-3 linkages or by any combination of α1-6 and α1-3 linkages. This protein may also be known as a "glucosyltransferase" (GTF) or a protein which has GTF activity. The polymer may contain at least two glucose residues and is referred to as a "dextran". A "dextransucrase gene" refers to the DNA sequence coding for a dextransucrase protein.

A "carbohydrate polymer," differing from true dextrans by consisting of glucose residues linked through alternating α1-6 and α1-3 linkages is referred to as "alternan". The protein product with the capability of catalyzing the reaction resulting in synthesis of an alternan is referred to as "alternansucrase". An "alternansucrase gene" refers to the DNA sequence coding for an alternansucrase protein.

The term "deleterious effect" as used herein refers to a direct or indirect injurious effect on a plant or plant cell as a result of fructan accumulation, such that the plant or plant cell is prevented from performing certain functions including, but not limited to, synthesis and transport of carbohydrates within a cell and throughout the plant, regeneration of transgenic plants or tissue, development of the plant or plant cell to maturity, or the ability to pass the desired trait or traits to progeny.

"Selective expression" refers to expression almost exclusively in specific organs of the plant, including, but not limited to leaves, tubers or seed. The term may also refer to expression at specific developmental stages in an organ, such as in early or late embryogenesis. In addition, "selective expression" may refer to expression in specific subcellular locations within the cell, such as the cytosol or vacuole.

The term "higher than native sucrose level" refers to a cell containing increased sucrose content over the natural range found in wild-type plant cells of the same species. The higher sucrose content may occur during any stage of cellular development, resulting from natural mutation or transgenic manipulation of a gene or genes within the cell. Increased sucrose may accumulate throughout the cell or in specific subcellular compartments. An example of a plant containing higher than native sucrose concentration includes, but is not limited to, the endosperm of standard sweet or super sweet lines, compared to native or "dent" corn. Sucrose concentration in maize lines, known as "dent" corn reaches a maximum level at 15–18 days after pollination, and accumulate up to 4–8% of the dry weight of the kernel. The sucrose concentration drops to a final concentration of 0.5–1.5% of the dry weight of mature dent kernels. High sucrose lines include, but are not limited to, standard sweet corn (su) and super sweet varieties (sh2, bt2, su/se, etc.). Sucrose content in a standard sweet variety reaches twice the level of dent at the same stage of development. Super sweet lines contain 3–4 times the level of sucrose compared to dent corn at the same stage of maturity.

The techniques of DNA recombination used throughout this invention are known to those skilled in the art and are generally described in Maniatis et al., Molecular Cloning: A Laboratory Manual, Cold Spring Harbor Laboratory, Cold Spring Harbor, N.Y. (1982).

Enzymatic Treatment of DNA

Restriction enzyme digestion buffers and digestion conditions used were those supplied by the manufacturer of each particular enzyme. Enzyme was added to give 5–10 units per microgram of DNA and the reaction mixture was adjusted to the appropriate final volume with water. Incubation of reaction mixtures at the appropriate temperature was for approximately 2 hours. DNA ligations were performed with amounts of vector and insert suggested as described in Maniatis et al., Molecular Cloning: A Laboratory Manual, Cold Spring Harbor Laboratory, Cold Spring Harbor, N.Y. (1982). Reaction conditions for DNA ligations were those described by the manufacturer of the T4 DNA ligase (Bethesda Research Laboratory, Gaithersburg, Md.).

Gel Electrophoresis of DNA

Agarose gel electrophoresis of DNA was performed in 0.7% agarose gels using Tris-Borate-EDTA (TBE) buffer, consisting of 89 mM Tris, 89 mM borate (pH 8.3) and 2.5 mM EDTA. Electrophoresis was conducted at a voltage of 50 to 150 volts depending on the amount of DNA per lane and the desired timing of the run. After electrophoresis, the gel was stained with 1 ug/ml of ethidium bromide and the DNA visualized on an ultraviolet transilluminator. DNA was recovered from gels using the materials and methods supplied in a Gene Clean kit purchased from BIO-101.

Plasmid Isolation and Purification

*E. coli* cells (HB101 frozen competent cells, purchased from BRL) containing transformed plasmids were grown overnight at 37° C. in 500 ml. LB media (10 g Bactotryptone, 5 g yeast extract and 10 g sodium chloride) containing 100 ug/ml ampicillin. Plasmid isolation and purification procedures were those described by the manufacture using a Promega Maxi-Prep DNA purification system.

BRIEF DESCRIPTION OF SEQUENCES LISTINGS

The invention may be more fully understood from the following detailed Sequences Descriptions which are part of this application. The Sequence Descriptions may contain single letter codes for amino acids as defined in 37 C.F.R. 1.822 which are incorporated herein by reference.

SEQ ID NO:1 is a partial nucleotide sequence of the *Bacillus amyloliquifaciens* SacB FTF gene. This 31 bp sequence spans the region of the prokaryotic signal cleavage site. SEQ ID NO:1 has been altered such that it contains a sequence recognition site for the DNA restriction enzyme EcoRV, beginning at nucleotide 13. Designed for use in site-directed mutagenesis of DNA, this nucleotide sequence will add a unique EcoRV site one codon 3' of the cleavage signal.

SEQ ID NO:2 is a partial nucleotide sequence of the tobacco SSU promoter region. The 21 bp nucleotide is 5' of the unique BglII site in the promoter region and is useful as a 5'-3' primer in subcloning a portion of the promoter region by PCR method.

SEQ ID NO:3 is a partial nucleotide sequence of the tobacco SSU promoter region. This sequence is a 3'-5' complement of the SSU promoter region and has been altered such that it contains the sequence recognition sites for the DNA restriction enzymes EcoRV and NcoI beginning at nucleotides 7 and 12, respectively. The ATG codon of the NcoI site in this 32 bp sequence is the initiation codon for the native SSU gene. This oligonucleotide sequence is designed for subcloning a portion of the SSU promoter, in a PCR reaction, when used in combination with the primer listed as SEQ ID NO:2.

SEQ ID NO:4 is a partial DNA sequence of the *Bacillus amyloliquifaciens* SacB FTF gene. The 21 bp oligonucleotide sequence corresponds to the region of the SacB gene 31 bp 3' of the prokaryotic cleavage signal and is useful as a PCR primer in detecting the presence of SacB gene(s) integrated into genomic DNA.

SEQ ID NO:5 is a partial DNA sequence of the *Bacillus amyloliquifaciens* SacB FTF gene. This sequence is a 3'-5' compliment of the conventional SacB DNA sequence. Beginning at nucleotide 1 of this 23 bp sequence is a recognition site for the DNA restriction enzyme SalI. The native SacB sequence begins at nucleotide 6. This oligonucleotide is designed to be used in a PCR reaction with SEQ ID NO:4.

SEQ ID NO:6 is a partial DNA sequence of the sporamin gene, (a sweet potato storage protein). This 142 bp sequence represents the N-terminal prepro- and pro-peptide of the vacuole targeting signal. The sequence has been altered such that the initiation codon is contained within a BspHI DNA restriction enzyme site, beginning at nucleotide 14. An SpeI DNA restriction enzyme site is coded for at nucleotides 1 through 6 and the recognition sites for restriction enzymes NcoI and XhoI are located at nucleotides 130–136 and 137–142, respectively.

SEQ ID NO:7 is a partial DNA sequence of the sporamin gene. This sequence is in a 3'-5' orientation, compared to the conventional DNA sequence and is a perfect compliment to SEQ ID NO:6. This oligonucleotide of 142 bp is designed to anneal to SEQ ID NO:6, creating a synthetic DNA cassette of the sporamin vacuole targeting DNA sequence, with the restriction enzyme recognition sites listed in the description for SEQ ID NO:6. The enzyme sites are useful for subcloning purposes.

SEQ ID NO:8 is an amino acid sequence of the sweet potato sporamin vacuole targeting peptide, coded for by the oligonucleotides listed in SEQ ID NO:6 and SEQ ID NO:7. The prepro-peptide begins at amino acid 1 and continues through amino acid 21. The pro-peptide represented by amino acids 22 through 37. The complete prepro-peptide, operably linked to the native or a foreign protein, will direct that protein into the vacuole of a plant cell.

SEQ ID NO:9 is a partial nucleotide sequence of a barley lectin gene, (Bednarak and Raikhel, The Plant Cell, 3:1195–1206 (1992); Dombrowski et al., The Plant Cell, 5:587–596 (1993)). This 56 bp sequence contains coding information for the C-terminal vacuole targeting sequence of barley lectin. The DNA sequence has been altered such that recognition sites for the restriction enzymes HincII and BglII are coded for at nucleotides 4–9 and 51–56, respectively.

SEQ ID NO:10 is a partial nucleotide sequence of the barley lectin gene. The 56 nucleotides of this sequence are a perfect complement to SEQ ID NO:9, such that annealing of the two creates a DNA fragment that allows digestion with restriction enzymes followed by subcloning into appropriate expression vectors.

SEQ ID NO:11 is the 15 amino acid sequence of the barley lectin, C-terminal, vacuole targeting peptide. This amino acid sequence is coded for by the oligonucleotides listed in SEQ ID NO:9 and SEQ ID NO:10. This peptide, operably linked to the native or a foreign protein, will direct the sorting of that protein from the ER, into the plant cell Vacuole.

SEQ ID NO:12 is a partial DNA sequence of the barley lectin gene, (Bednarak and Raikhel, The Plant Cell, 3:1195–1206 (1992); Dombrowski et al., The Plant Cell, 5:587–596 (1993)). The 38 bp sequence is useful as a PCR primer in obtaining the N-terminal secretory signal of the barley lectin gene. This primer anneals to the 5' end of the signal sequence and contains a recognition site for the restriction enzyme EcoRI beginning at nucleotide 7. The EcoRI site is useful for subcloning purposes. The sequence also contains a recognition site for BspHI at nucleotides 14–19. This site is useful for subcloning DNA fragments in frame with the initiation codon located at nucleotides 16–18.

SEQ ID NO:13 is a partial DNA sequence of the barley lectin gene. This 38 bp sequence is useful as a PCR primer for cloning the N-terminal secretory signal of the barley lectin gene. The recognition sequences for SalI and NcoI restriction enzymes are coded for at nucleotides 1 through 6 and 6 through 11, respectively. This DNA sequence is a reverse compliment of the barley lectin DNA and is designed for use in a PCR reaction, with the primer listed in SEQ ID NO:12. A DNA fragment recovered from a PCR reaction using the primers of SEQ ID NO:12 and SEQ ID NO:13, is sufficient for direction of the native or an operably linked foreign protein into the secretory system of plant cells.

SEQ ID NO:14 is a partial DNA sequence of the potato tuber specific, patatin protein. The 20 bp sequence corresponds to the promoter region 1.0 Kb 5' of the initiation codon.

SEQ ID NO:15 is a partial DNA sequence of the potato tuber specific, patatin protein. The 22 bp sequence is a reverse compliment of the patatin DNA sequence and when included in a PCR reaction with the primer listed in SEQ ID NO:14, a 1.0 Kb DNA fragment, may be obtained which contains the necessary regulatory sequences for tuber specific gene expression. The sequence contains the recognition site for a NcoI restriction enzyme including the native initiation codon (nucleotides 1 through 6).

SEQ ID NO:16 is a partial DNA sequence of the high sulfur zein storage protein, (Kirihara et al., Gene, 71:359–370 (1988)). The 25 bp DNA sequence contains a recognition site for the restriction enzyme EcoRV beginning at nucleotide 20.

SEQ ID NO:17 is a partial DNA sequence of the high sulfur zein storage protein. This 30 bp sequence contains a recognition site for the restriction enzyme XbaI located at nucleotides 6 through 11. SEQ ID NO:16 and SEQ ID NO:17 are designed to be used together in a PCR reaction such that a 1.4 Kb DNA fragment, containing a portion of the 10 Kd zein promoter region and coding sequence may be isolated and subcloned into a suitable vector, using the restriction sites EcoRV and XbaI.

SEQ ID NO:18 is a partial DNA sequence of the high sulfur zein storage protein. This 30 bp DNA sequence is designed for use in a PCR reaction such that a portion of the 10 Kd zein gene may be obtained.

SEQ ID NO:19 is a partial DNA sequence of the high sulfur zein storage protein. The 32 bp of this DNA sequence contain a BamHI restriction enzyme recognition site located at nucleotides 6 through 11. SEQ ID NO:18 and SEQ ID NO:19 are designed to be used as a set of PCR primers, such that a 1.39 Kb DNA fragment containing a portion of the zein gene may be obtained. The DNA fragment may be subcloned into an appropriate vector using a blunt restriction enzyme site and the BamHI site.

SEQ ID NO:20 is a partial DNA sequence of the high sulfur zein storage protein. The DNA consists of 13 bp and is designed as a adapter, such that a unique SmaI restriction enzyme recognition site may be added to the coding region of the 10 Kd zein gene. The SmaI recognition site begins at nucleotide 5 of this DNA sequence.

SEQ ID NO:21 is a partial DNA sequence of the high sulfur zein storage protein. The 13 bps of this DNA sequence are a partial compliment to the DNA sequence of SEQ ID NO:20. The two DNA sequences, annealed create a unique SmaI restriction enzyme recognition site, useful for subcloning purposes.

DETAILED DESCRIPTION OF THE INVENTION

The subject matter of this invention includes methods for transforming a plant cell with an expression cassette containing appropriate regulatory and targeting sequences, resulting in accumulation of fructan in the vacuole of seeds or tubers of the mature plant. The expression cassette includes a promoter region. The preferred promoter regions are the tissue specific 10 kD Zein promoter and the tissue specific patatin promoter region. The promoter region is functionally linked to the coding region of a chimeric protein consisting of a vacuolar targeting sequence and an enzyme capable of polymerizing fructose. The preferred vacuolar targeting signal is derived from the first 30 amino acids starting at the NH-terminal of the sweet potato storage protein, sporamin and the N-terminal and C-terminal sequences necessary for targeting the Barley lectin protein to the vacuolar compartment. Either the Sporamin or the Barley lectin vacuole targeting sequences are sufficient for directing a protein to the endoplasmic reticulem (ER), sorting within the ER, and transferring to the vacuole via the Golgi apparatus. The vacuole targeting sequences are fused, in frame to the mature coding region of the *Bacillus amyloliquefaciens* FTF protein.

The subject matter of the invention includes a monocot or dicotyledonous plant transformed with at least one copy of the claimed cassette with the preferred plants being corn or potato. Seed or tubers from the plants are also claimed.

The subject mater of the invention also includes a method for accumulating fructans in monocot or dicotyledonous plants comprising:

(a) transforming a plant cell with the described cassette containing the *Bacillus amyloliquefaciens* FTF gene linked to a vacuole targeting signal and suitable 5' and 3' seed or tuber specific transcription regulatory sequences;

(b) growing fertile, sexually mature plants from the transformed plant cell; and (c) selecting progeny seed or tubers from the fertile plants of step (b) for accumulated fructan within those tissues.

The present invention describes a set of chimeric genes comprising tissue specific regulatory sequences, vacuole targeting sequences and a bacterial FTF coding sequence. The chimeric gene is capable of synthesizing a fructose polymer using sucrose as a substrate when expressed in a transgenic monocot or dicotyledonous plant. A transgenic corn plant (*Zea mays*), or potato (*Solanum tuberosum*), or tobacco (*Nicotiana tabacum*), properly expressing the FTF gene, distinguishes itself from a generic plant of the same species by the presence of fructan accumulated in mature seeds, tubers or leaves.

Transfer of the nucleic acid fragments of this invention into a plant directs expression of the protein in a manner that results in accumulation of this useful polymer, without concern for loss or alteration of the polymer due to plant degratory enzymes during harvest, transport, or storage and without the loss of established co-products from any particular species. Transgenic crops containing chimeric genes comprising tissue specific regulatory sequences, vacuole targeting sequences, and a bacterial FTF gene will provide a renewable source of large molecular weight fructose polymers. Accumulation of fructan will be determined in part, by: (1) the level of expression of the chimeric gene in transformed crops. The level of expression depends in part, on the tissue specific expression signals, the number of copies of the gene integrated into the plant genome and location of gene integration. (2) Fructan accumulation may also be subject to the amount of substrate available. The amount of substrate available to the enzyme depends on the species (including mutants within a species), the tissue type where expression occurs, the subcellular location of expression and on the stage of development of a particular plant. (3) The stability of the introduced protein may also influence fructan accumulation and depends in part, on its proper processing, intracellular targeting and its ability to function in a foreign environment.

A principle objective of this invention is to utilize sucrose produced as the result of photosynthesis and stored in the vacuole of plant cells in order to accumulate fructans in transgenic *Zea mays* seed, tubers of *Solanum tuberosum*, or leaves of *Nicotiana tabacum* via introduction of a bacterial FTF gene with appropriate tissue specific and intracellular localization (e.g., vacuole) regulatory sequences.

Successful expression of a gene with carbohydrate metabolic properties such as the *B. amyloliquefaciens* FTF gene, in a transgenic plant would require consideration of the following factors: (1) the species transformed, (2) the specific tissue where expression is to occur, (3) the timing of expression, (4) and the subcellular location of gene expression. All of these factors must be carefully coordinated in order for production of fructan to occur in a transgenic cell, with no deleterious effect.

Expression of a gene with sucrose metabolizing activity, such as a bacterial FTF protein in one particular transgenic species will not necessarily create the same desired effect when expressed in another. Differences in carbohydrate profiles among species suggests that an enzyme specific for sucrose will not always have sufficient substrate available to produce the same result when expressed in various species. Availability of sucrose as a substrate not only varies greatly from species to species but also in mutants within the same species, (Lampe, Bot. Gaz., 91:337–380, (1931)). Although most plants synthesize and translocate sucrose it is not true that all plants follow this strategy for moving carbon to nonphotosyntheic tissues. For example, many plants species synthesize and translocate alditols. Mannitol is synthesized in the leaves of celery, *Apium graveolens* and translocated via the phloem where it is stored in the petiole (Rumpho et al., Plant Phys., 73:869–873, (1983)). Another example are the Cucurbitaceae, where raffinose saccharides are the predominant transport sugar (Hendrix, Plant Sci. Lett., 25:1–7, (1982); Webb and Gorham, Plant Physiol., 39:663–672 (1964)). Therefore, the amount of fructan produced by a bacterial FTF will be influenced by the level of alternate carbohydrates present, as well as the level of sucrose, which differs greatly among species.

Mechanisms for sucrose transport and accumulation in sink tissue also vary greatly from one species to another. Sucrose hydrolysis is an integral part of the import mechanism in developing corn seed, (Porter et al., Plant Phys., 77:524–531 (1985)), but does not appear to be a prerequisite for transport to soybean seed (Thorne, Plant Phys., 70:953–958 (1982)), or to wheat endosperm, (Jenner, Aust. J. Plant Phys., 1:319–329 (1974)). Expression of a FTF in the seed of one species may result in the protein having access to an abundance of sucrose, but fructan synthesis in seed of other species would be hindered by the presence of predominantly hexoses sugars.

Another useful illustration of the role a plant species plays in accumulated carbohydrate profile would be in the comparison of sugars found in sink tissue of plants such as tomato fruit or potato tubers. Domesticated tomato fruit tissue accumulates primarily hexose due to the activity of three separate invertase enzymes. The soluble acid invertase located in the vacuole of tomato fruit and an invertase associated with the cell wall are primarily responsible for accumulation of hexose throughout this tissue. A cytosolic alkaline invertase has also been described in tomato (Yelle et al., Plant Phys., 95:1026–1035 (1991)). Alternatively, the primary sink tissue of potato, developing tubers, are devoid of invertase activity. Sucrose is transported to potato tubers intact, (as is true in tomato fruit), but hydrolysis is held to a minimum by expression of an irreversible protein inhibitor of invertase in tubers (Pressey, Arch. Biochim. Biophys., 113:667–674 (1966)). Hydrolysis of sucrose in tuber cells is further limited by the low activity of cytosolic sucrose metabolic enzymes. Because of this, much of the sucrose is stored in vacuoles and remains unhydrolyzed until metabolized for starch synthesis, (Oparka et al., Planta, 182:113–117 (1990)).

von Schaewen et al., (EMBO J. 9:3033–3044, (1990)) reported that expression of a yeast invertase gene under the direction of a constitutive plant promoter, the CaMV 35S promoter, resulted in a different phenotype when transformed into tobacco compared to that in transgenic *Arabidopsis thaliana*. The cassette used for invertase expression in tobacco, (von Schaewen et al., EMBO 9:3033–3044 (1990)) was also used to transform potato. Transgenic potato leaves also responded differently than the previous examples, possibly due to the differences in sink capacity compared to tobacco and Arabidopsis (Heineke et al., Plant Phys. 100:300–308 (1992)). Because source-sink relationships are known to differ among species, it is not unreasonable to think that disruption of this relationship would have different effects depending on the species of plant where the chimeric invertase gene was expressed.

If the species of plant affects the successful expression of a FTF protein, the tissue type within a species also has considerable bearing on the production of fructan and ultimately how the plant will react to accumulation of this polymer. The growth and development of a plant is critically dependent on the energy gained by fixing carbon dioxide into carbohydrate during photosynthesis. In higher plants, leaves and to a certain extent the stem, represent the primary site for photosynthesis. In contrast, other parts of the plant (e.g., roots, seeds, or tubers), do not contribute significantly to carbohydrate synthesis, but rather are largely dependent on carbon dioxide fixed in the photosynthetically active tissues. Thus there is an energy flow from tissues that are net exporters (sources) to tissues that are net importers of fixed carbon (sinks). In most plants sucrose is the preferred carbohydrate for transport of photoassimilates from source to sink tissue. Transport of sucrose to sink regions in many plants involves an active transport step, (Daie, Plant Mol. Biol. Rep., 7:106–115 (1989)). This transport system is specific for sucrose therefore, hexose sugars are not efficiently mobilized, but are reabsorbed by mesophyll cells surrounding the phloem (Maynard and Lucas, Plant Phys., 70:1436–1443 (1982)). Hydrolysis of sucrose interferes with carbohydrate distribution throughout a plant, resulting in a profound negative effect on the tissues most dependent on imported energy. The interaction of this sink-source relationship is not only central to plant development, but also plays a crucial role in crop yield (Turgeon, Ann. Rev. Plant Physio. Plant Mol. Bio. 40:119–138 (1989)).

Examples of the detrimental effect of expressing a yeast invertase gene, (hydrolyzing sucrose) in source tissue of transgenic plants has been reported (Dickinson et al., Plant Physiol 95:420–425 (1991); Ding et al., The Plant J., 4:179–189 (1993); Stitt et al., Planta 183:40–50 (1990); von Schaewen et al., EMBO J., 9:3033–3044 (1990)). Expression of yeast invertase in the apoplast offers a unique opportunity to interfere with, and characterize sink-source relationships. Constitutive expression, in source tissue, of the invertase gene fused to an apoplast targeting sequence, led to severe stunting, increased starch, glucose and fructose accumulation in leaves, decreased photosynthetic activity and suppressed root development in transgenic tobacco (von Schaewen et al., EMBO 9:3033–3044 (1990)), and tomato (Dickinson et al., Plant Phys. 95:420–425 (1991)). In potato the yeast invertase gene disrupted sucrose transport leading to symptoms very similar to water stress and ultimately led to a significantly reduced tuber yield (Heineke et al., Plant Phys. 100:300–308 (1992)). Each case demonstrates that preventing carbon transport in a plant by expression of a sucrose hydrolytic enzyme in source tissue results in restricted development of sink tissue. Stitt et al., (Planta, 183:40–50 (1990)), also demonstrated that interference with sucrose transport in tobacco leaves led to accumulation of carbohydrate in that tissue, which in turn caused photosynthetic activity to be down-regulated.

Timing the expression of sucrose metabolizing proteins must take into consideration the change in sucrose concentration that occurs during plant development. The importance of sucrose within tissue also changes with time. For example, the role of sucrose in a sink leaf is quite different than in a source leaf. Sucrose is metabolized in sink leaves to support growth. However, as a leaf matures it becomes a net exporter of sucrose. Less critical to the maintenance of the leaf, sucrose is transiently stored in the vacuole and then transported to sink regions via the phloem. Sink tissue also undergoes changes in sucrose concentrations during development. Sucrose concentration in sweet melons for example, changes as the fruit matures. Hexose sugars accumulate early in development, followed by high levels of sucrose at later stages (Schaffer et al., Phytochemistry, 26:1883–1887 (1987)). In contrast, sucrose content falls dramatically in pea seed with continued development (Holl and Vose, Can. J. Plant Sci., 60:1109–1114, (1980)). Sucrose concentration in developing corn endosperm increases from 8 to 12 days after pollination and then drops more than ten fold 28 days after pollination (Tsai et al., Plant Phys., 46:299–306, (1970)). Sucrose concentration in soybean seed changes significantly during development as raffinose saccharides content increases dramatically, 53 days after anthesis (Amuti, Phytochemistry, 16:529–532, (1977)). Altered carbohydrate profile during development as demonstrated in the examples listed above, illustrate the importance of promoter selection for specific expression of a gene in the desired tissue and timed to take advantage of fluctuating sucrose pools.

The subcellular location of sucrose metabolic enzyme expression such as an invertase or FTF protein may also have a dramatic effect on the transgenic line. Plants expressing a yeast invertase in either the cytosol, vacuole or the apoplast demonstrated a distinct phenotypic difference with respect to subcellular location of expression. Transgenic tobacco is much more sensitive to expression of invertase in the cytosol compared to the apoplast. This result suggests that expression of sucrose metabolic enzymes in the cytosol interferes with sucrose synthesis (Sonnewald et al., The Plant Journal, 1:95–106 (1991)). Phenotypes reported in tobacco expressing yeast invertase in the vacuole of leaves were less dramatic, suggesting that sucrose stored transiently in the vacuole of leaves, is less metabolically active compared to the cytosolic pool.

Photoassimilate partitioning between different cellular compartments within a cell is one of the central determinants of plant growth and development. The results obtained by expressing a sucrose metabolizing enzyme in various compartments of a transgenic plant clearly demonstrate the importance of compartmentalization of sucrose and of protein targeting in plant development and metabolism. Phenotypic differences that may reflect the varied role of sucrose in different cellular compartments are noted by Sonnewald et al. (J. Exp. Bot., 44:293–296 (1993)). This study also demonstrates phenotypic and biochemical differences that develop in transgenic plants expressing the yeast derived invertase in either the cytosol, the apoplast or the vacuole. The differences vary with the compartment in which the invertase is expressed.

Cytosolic expressed invertase in tobacco resulted in thick curled leaves, possibly due to a more rapid expansion of the upper surface of the leaf than of the lower. The same promoter and gene now targeted to the vacuole or apoplast demonstrated symptoms only in older leaves where bleached and necrotic regions developed. In addition to phenotypic differences younger leaves of vacuole targeted transgenic plants showed no noticeable symptoms however photosynthesis was slightly higher than in wild-type controls. Photosynthesis in cytosolically targeted invertase plants was determined to be lower than the rates found in controls. Transgenic plants are very sensitive to invertase in the cytosol compared to cell wall expressed invertase. Cytosolic invertase in a source cell interferes directly with sucrose synthesis, while apoplastic invertase will prevent sucrose transport. Invertase expression in the vacuole may also interfere with eventual sucrose transport and indicated that the exchange of sucrose between the vacuole and cytosol of leaves may be quite high. Due to its role in carbon translocation throughout the plant, sucrose is found in most tissues and in many subcellular compartments. The role sucrose plays in the various location is not always identical. Compartmentation may play a role in sequestering sucrose from metabolic enzymes prior to transport, it may serve as a temporary storage site for sucrose while demand is limiting, or long-term storage in certain species such as sugarcane or sugar beet.

Clearly, a generalized statement concerning the effectiveness of a transformed sucrose metabolic protein such as a bacterial FTF in any plant species, in any tissue within the plant, with no regard for developmental timing of expression and without concern for subcellular location of expression would be grossly inaccurate. Expression of a sucrose metabolic protein throughout the plant with a constitutive promoter as demonstrated in tomato, (Dickinson et al., Plant Phys. 95:420–425 (1991)) may be particularly harmful. Prevention of photoassimilate transport in tomato led to deformation of leaves and severe growth inhibition. Successful expression of metabolic enzymes of this type must be controlled by appropriate tissue specific promoters with developmental timing needed to access appropriate sucrose pools. Subcellular targeting signals are also critical for the same reason. Selective combination of promoters, targeting signals and the species transformed all interact to bring about the successful accumulation of desired product without serious detriment to the plant. There has yet to be described the successful expression of a heterologous sucrose metabolic enzyme such as a bacterial FTF, however it is abundantly clear from the discussion above that expression of such a protein in an indiscriminate manner will not guarantee the production of a desirable plant.

A bacterial FTF gene from *Streptococcus mutans*, transferred into tomato, has been reported, (Patent application PCT #WO 89/123486). The expression cassette used in this report, contains a mannopine synthase promoter. Mannopine synthase, from *Agrobacterium tumefaciens*, is constitutively expressed in a wide variety of plants (Barker et al., Plant Mol. Biol. 2:335–350 (1983)). The promoter is not known to be tissue specifically regulated in any plant tissue or species. Of the 19 transformed plants containing the bacterial FTF cassette in this patent application, all but one transformant resulted in disruption of the gene upon integration. This resulted in production of truncated RNA transcripts and would not be expected to produce a protein with viable FTF activity. One line apparently produced full length RNA, but no data demonstrating FTF activity was presented. It is likely that FTF expression in the cytosol of cells throughout the transgenic tomato plant is detrimental to growth and development of tissue, as was demonstrated for the yeast invertase gene in tobacco (Sonnewald et al., The Plant J., 1:95–106 (1991)). Prevention of photoassimilate transport to sink tissues may have contributed to the low level success rate of transformation. Selection against active expression may explain the apparent gene rearrangement demonstrated in this work. A point mutation or deletion of only a few bases, not uncommon in situations where expression of the gene is detrimental to the tissue, could lead to a transformant which produces an apparent full length RNA but, would not be translated into a functional FTF protein.

Expression of a GTF in the apoplast of tomato was also considered in the patent application PCT #WO89/12386. Although plants were recovered, there was no information reported on the activity of the protein in transgenic tissue. This may have been due to the detrimental effect of carbohydrate polymer synthesis in the apoplast of a tomato cell. Expression of a yeast invertase in the apoplast of leaves or stem was demonstrated to be disruptive to the flow of carbon and tissue development in tomato and tobacco (Dickinson et al., Plant Phys. 95:420–425 (1991); (von Schaewen et al., EMBO J. 9:3033–3044 (1990)). The argument for causing detrimental effects, due to disruption of carbon transport by expression of a GTF or FTF in source tissue of tomato, would be no different than those reported for yeast invertase.

If expression of sucrases in the manner described, had been possible, there would be no reason to expect that the result would be the same for expression in other species. Apoplastic expression of a sucrose metabolic enzyme in various tissues such as corn endosperm may be expected to have little effect due to the minimal sucrose content in this compartment (Shannon, Plant Phys., 49:203–206 (1972); Shannon, Plant Phys., 49:198–202 (1972); Felker and Shannon, Plant Phys., 65:864–870 (1980)). Expression of an FTF in the apoplast of potato tuber would have access to sucrose, but would also be expected to result in severe inhibition of that tissue. Oparka and Wright (Planta, 175:520–526 (1988)), have shown that sucrose is translocated to tuber cells in tact, and that alteration in osmotic potential, by means such as the hydrolysis of sucrose has a critical effect, preventing sucrose from reaching the developing tuber (Oparka and Prior, Plant Cell Env., 10:667–675 (1987); Oparka and Wright, Planta, 174:123–126 (1988)).

To provide for accumulation of fructose polymers in a plant cell where native cells do not synthesize polymers of this type, and where the expression is not substantially destructive to the tissue, an expression cassette should include a transcriptional and translational initiation region which functions in specific plant cells; a coding sequence for a FTF gene, preferably including targeting sequences in the correct reading frame at the 5' or 31 terminus, where the targeting sequences direct the FTF protein to the endoplasmic reticulem, the Golgi apparatus and then to the vacuole of the cell; in addition to a transcriptional termination region.

A FTF is intended to mean an enzyme with fructose polymerase activity. Preferred is the extracellular FTF, levansucrase EC 2.4.1.10. The FTF gene may be derived from microbial sources. For example, genes for levansucrase which polymerize the fructose residue of sucrose to form levan may be obtained from various species including, but not limited to, *Aerobacter levanicum*, (Evans and Hibbert, Adv. Carbohydr. Chem., 2:253–277 (1946)); *Bacillus subtilis*, (Dedonder, Methods Enzymol., 8:500–505 (1966)); *Bacillus polymyxa*, (Hestrin et al., Biochem. J., 37:450–456 (1943)); *Streptococcus salivarius*, (Fuchs, Nature, 178:921 (1956)) or *Microbacterium levaniformus*, (Fuchs et al., Antonie van Leeuwenhoek 51:333–351 (1985)). The preferred FTF coding sequence that will enable this invention is derived from *Bacillus amyloliquifaciens* (Mantsala and Puntala, FEMS Microbiol. Lett., 13:395–399 (1982); Tang et al., Gene, 96:89–93 (1990)).

The source of the FTF gene is not critical so long as it accomplishes the purpose of the invention which is to synthesize and accumulate large molecular weight fructose polymers in a transgenic plant cell. The FTF protein in this invention, utilizes sucrose, the major metabolite resulting from photosynthesis in most plants. This being true, anyone skilled in the art may substitute a protein which utilizes sucrose in the catalysis of a carbohydrate polymer. A group of such proteins, known as sucrases include, but are not limited to levansucrase, alternansucrase or one of many dextransucrases (Abo et al., J. Bact., 173:989–996 (1991); Gilmore et al., Infec. and Immun., 58:2452–2458 (1990); Cote, Carbo. Poly. 19:249–252 (1992); Giffard et al., J. Gen. Micro., 139:1511–1522 (1993)). Having similar properties to FTFs, proteins such as dextran-sucrases and alternansucrase would be expected to perform in a similar fashion when expressed in transgenic plants. Sucrases may be considered a set of similar proteins in that they each acts as a monomer, using sucrose as the sole substrate, requiring no additional cofactors, while catalyzing the polymerization of a hexose residue.

Dextransucrase proteins catalyze the formation of glucose polymers containing $\alpha$1-3, $\alpha$1-6 or combinations of $\alpha$1-3 and $\alpha$1-6 linked glucose residues. Dextran-sucrase genes from various sources or different but related genes from the same microorganism determine the type of linkage and the pattern of branches within the polymer. The type of glucose linkage and the pattern of linkages is directly related to the properties of the polymer. For example, polymers consisting of predominately $\alpha$1-3 linked glucose residues are insoluble in water, while those that are predominately $\alpha$1-6 are very soluble (Walker Int. Rev. in Biochem., 16:75–126 (1978); Rolla et al., Special Supp. to Chem. Sci., pp. 21–29, Doyle and Ciardi eds., (1983)). Alternans are unique dextrans consisting of glucose linked in alternating $\alpha$1-3 and $\alpha$1-6 linkages (Miasaki et al., Carbo. Res., 84:273–285 (1980)). Alternans posses a low intrinsic viscosity very much like gum arabic which is in great demand for its use as a noncaloric bulking agent. The high price and short supply of gum arabic has led to a search for a substitute. Alternans, produced at competitive cost would be an excellent replacement for gum arabic and may find additional uses as the price and availability allows.

Dextrans are currently produced on a commercial scale by fermentation culture, only for high value use, such as in scientific research and as a blood plasma extender. Accumulation in transgenic plants would increase availability and reduce cost for existing products, and reduced costs would potentially open new markets for these novel polymers. Uses would be determined by unique properties. The pattern of glucose linkage and number of branches determines starch function, and ultimately use. Dextrans and alternans contain unique glucose linkages, not found in starch molecules and therefore, may be useful in products not open to natural or modified starches.

Proper expression levels of the FTF gene or any of the sucrase genes, may require the use of various chimeric expression cassettes containing different promoters. The expression of foreign genes in transgenic plants is well established (De Blaere et al., Meth. Enzymol. 143:227–291 (1987)). Preferred in this invention is expression of the FTF gene in seeds, tubers and leaves derived from corn, potato and tobacco, respectively. Tissues, including seed and tuber from plants including, but not limited to sugar beet, sugarcane, Jerusalem artichoke, chicory and canola may also be transformed, such that they accumulate this, or related carbohydrate polymers, (i.e., dextrans and alternans).

The species chosen as the source for a promoter necessary to regulate FTF expression is not critical so long as the promoter has sufficient transcriptional activity to accomplish the invention by expressing the FTF gene in the desired host and tissue type. Preferred promoters are those that allow expression of the protein specifically in the seed, tuber or the leaf. Examples of seed specific promoters include, but are not limited to the promoters of seed storage proteins. These storage proteins are strictly regulated, resulting in exclusive expression in seed tissue. Strict regulation may be critical for optimum expression or when action on a specific substrate pool is desirable. Expression of seed storage proteins is highly organ-specific in addition to stage specific (Higgins et al. Ann. Rev. Plant Physiol., 35:191–221 (1984); Goldberg et al. Cell, 56:149–160 (1989); Thompson et al., Bioessays, 10:108–113 (1989)). Different seed storage proteins may be expressed at different stages of development. There are presently numerous examples for seed-specific expression of storage proteins in transgenic dicotyledonous plants. These include genes for the soybean lectin (Okamuro et al., Proc. Natl. Acad. Sci. USA, 83:8240–8244 (1986), pea legumin (Shirsat et al., Mol. Gen. Genet., 215:326 (1989), and rape seed napin (Radke et al., Theor. Appl. Genet., 75:685–694 (1988)).

Seed specific promoters, operably linked to heterologous coding sequences in chimeric gene constructs, have been shown to maintain their temporal and spatial expression pattern in transgenic plants. Examples include the *Arabidopsis thalina* 2S seed storage protein promoter used to express enkephalin peptides in seeds of the transgenic species Arabidopsis and *B. napus* (Vandekerckhove et al., Biotechnology, 7:929–932 (1989)). The bean lectin and bean β-phaseolin promoters, expressing the luciferase gene have been demonstrated to function properly when transformed into transgenic tobacco lines (Riggs et al., Plant Sci., 63:47–57 (1989)).

The major seed storage proteins in maize are a family of alcohol-soluble polypeptides known as the zeins. They consist of several separate classes distinguished by size when run on an SDS-polyacrylamide gel. The zein family of genes are synthesized on the rough endoplasmic reticulem specifically in maize endosperm cells during a period of between 12 and 50 days after pollination (Larkin and Hurkman, Plant Phys., 62:256–263 (1978)). The highly regulated, tissue specific expression and relative high RNA transcription level are reasons why the zein promoters are particularly attractive for expression of heterologous genes in transgenic corn endosperm cells. Several zein proteins have been identified (Pederson et al., J. Biol. Chem., 261:6279–6284 (1986); Das and Messing, Mol. Cell Biol., 7:4490–4497 (1987); Hiffman et al., EMBO, 6:3213–3221 (1987)). The preferred promoter for seed specific expression of the nucleic acid fragment of this invention will be the promoter from the 10 kD Zein seed storage protein, Kirihara et al., Mol. Gen. Genet., 211:477–484 (1988); Kirihara et al., Gene, 71:359–370 (1988)).

Preferred promoters for transgenic potato are those that allow tissue specific expression of the FTF gene in the tuber. Examples of tuber specific promoters include, but are not limited to the promoters of granule-bound starch synthase genes (Visser et al., Plant Mol. Bio., 17:691–699 (1991)), the starch branching enzyme, Koβmann et al., Mol. Gen. Genet., 230:39–44 (1991)), and the storage protein, patatin (Rocha-Sosa et al., EMBO J. 8:23–31 (1989)). Tuber specific promoters, operably linked to heterologous coding sequences have been shown to maintain their temporal and spatial expression in transgenic plants. Examples include the granule-bound starch synthase promoter used to direct the expression of the GUS marker gene (Visser et al., Plant Mol. Biol., 17:691–699 (1991); van der Steege et al., Plant Mol. Biol., 20:19–30 (1992)), and the patatin promoter, used to direct the expression of the CAT marker gene (Twell et al. Plant Mol. Biol. 9:345–375 (1987)), in addition to the GUS gene (Wenzler et al., Plant Mol. Biol. 12:41–59 (1989)).

Of particular use for tuber specific gene expression is the patatin promoter which has been well characterized in terms of defining the regulatory sequences involved in conferring tissue and developmental specific expression, (Mignery et al., Nuc. Acids Res., 12:7987–8000, (1984); Jefferson et al., Plant Mol. Biol. 14:995–1006 (1990); Twell et al. Plant Mol. Biol. 9:345–375 (1987)). Especially preferred for direction of gene expression in potato is a class I patatin promoter. This promoter has been characterized in great detail regarding tissue specific and developmental expression. Tight regulation of gene expression is desired for utilization of sucrose only in storage tissue, such as tuber, therefore class I patatin promoters expressed in tubers are particularly useful, while class II promoters also expressed in roots, would be less desirable (Pikaard et al., Nuc. Acids Res., 15:1979–1994 (1987)). Especially preferred is a truncated version of the Class I patatin promoter, encompassing 1.0 Kb upstream of the transcription initiation site. Two tissue specific elements have been identified in this patatin promoter fragment, one between −40 and −400 bp, the other between −400 and −957 bp of the transcription initiation site. These two elements are sufficient to confer tuber specific expression on a chimeric gene containing the truncated patatin promoter fused to the GUS marker gene (Jefferson et al., Plant Mol. Biol. 14:995–1006 (1990)). A truncated version of the patatin promoter consisting of a fragment from −40 to −957 bp from the transcription initiation site was shown to confer tuber specific expression on a truncated version of the cauliflower mosaic virus promoter, a promoter shown to be expressed throughout the plant in its native state (Jefferson et al., Plant Mol. Biol. 14:995–1006 (1990)).

Promoters capable of general expression in tobacco leaves have been identified. The promoter of the small subunit of ribulose-bis-phosphate carboxylase (SSU) gene is one example (Mazur and Chui, Nuc. Acids Res., 13:2373–2386 (1985)). Alternatively, the Cauliflower Mosaic Virus (CaMV) 35S promoter is preferred for expression in tobacco, primarily leaf tissue. The sequences necessary for general expression of the CaMV 35S promoter within tobacco tissue have been reported (Odell et al., Nature 313:810–812, (1985)). The CaMV 35S and SSU promoters have been demonstrated to be effective in directing expression of heterologous genes not only when transformed in native species, but across more plant species than any other promoters tested, to date.

Sucrose synthesis occurs, and is metabolized in the cytosol of a plant cell. Sucrose is a building-block in the production of a vast number of cell structures or products. Although deposited in the vacuole, it may be only intermittently during the overall development of the cell or stored, somewhat long term, as is the case in sugar beet. Vacuolar sucrose is not metabolically active (it is not utilized within the vacuole as a metabolite for the production of any cellular product), and therefore utilization for the purpose of fructan synthesis may be far less detrimental to the plant then would be by depletion of the cytosolic sucrose pool. Use of vacuolar sucrose may be accomplished by targeting the FTF gene to the vacuole of a transgenic cell.

The plant cell vacuole, part of the secretory system, performs numerous functions vital to cellular growth and development including accumulation of amino acids, inorganic ions and metabolic intermediates, e.g., glucose, fructose and sucrose. Many of these compounds enter the vacuole by protein based-channels or by active transport (reviewed by Matile, Ann. Rev. Plant Physiol. 29:193–213 (1978); and Wink, J. Exp. Bot. 44:231–246 (1993)). Proteins destined for the vacuole do not enter by simple diffusion nor do they enter by direct transport across the tonoplast. An N-terminal signal coded for in vacuole specific proteins first directs them to the rough endoplasmic reticulem (ER). The signal is cleaved in the ER subsequent to the ER fusing with the Golgi apparatus, where the protein is further processed. Vacuole targeting of proteins is determined by a secondary amino acid sequence located at either the N or C-terminal of the protein (Chrispeels, Ann Rev. Plant Phys. and Plant Mol. Biol. 42:21–53 (1991); Chrispeels and Rahikael, Cell 68:613–616 (1992)). This sequence allows the protein to be sorted in the Golgi. Golgi-derived vesicles containing the protein, detect and fuse with the tonoplast, depositing the protein into the vacuole (Neuhaus et al., Proc. Natl. Acad. Sci., 88:10362–10366 (1991); Bednarek and Raikhel, The Plant Cell, 3:1195–1206 (1991); Chrispeels, Ann. Rev. Plant Physiol. and Plant Mol. Biol., 42:21–53 (1991)).

Many vacuole targeting sequences have been identified including, but not limited to, tobacco chitinase A (Neuhaus et al., Proc. Natl. Acad. Sci., 88:10362–10366 (1991)), barley aluerain (Holwerda et al., Plant Cell, 4:307–318 (1992)), tobacco β-1-3 glucanase (Melchers et al., Plant Mol. Biol. 21:583–593 (1993)), and patatin (Sonnewald et al., The Plant J., 1:95–106 (1991)).

The preferred vacuolar targeting sequences of this invention are derived from the sweet potato root storage protein, sporamin and the barley lectin gene. The sporamin protein is synthesized as a prepro-peptide with an N-terminal sequence only. The N-terminal sequence includes a 21 amino acid signal pre-peptide and an additional pro-peptide of 16 amino acids responsible for entering the ER and sorting to the vacuole (Matsuoka and Nakamura Proc. Natl. Acad. Sci., 88:834–838 (1991)). The barley lectin gene contains separate signals at the N and C-terminal ends for targeting to the ER and vacuolar sorting in the Golgi, respectively (Bednarek and Raikhel, The Plant Cell, 3:1195–1206 (1992); Dombrowski et al., Plant Cell, 5:587–596 (1993)).

Vacuolar specific proteins have been demonstrated to be correctly targeted to the vacuole in heterologous transgenic plants (Bednarak et al., Plant Cell, 2:1145–1155 (1990); Matsuoka and Nakamura, Proc. Natl. Acad. Sci. 88:834–838 (1991); Holwerda et al., Plant Cell, 4:307–318 (1992)). Demonstration of correct assembly, processing and targeting of the vacuole specific barley lectin protein in tobacco, indicates that the sorting machinery in monocots and dicots is very similar (Wilkins et al., Plant Cell 2:301–313 (1992)). Furthermore, targeting sequences from vacuole specific genes, operably fused to heterologous coding sequences in chimeric gene constructs, also maintain the vacuole specific expression in transgenic plants. Such examples include the patatin vacuole targeting sequence fused to the yeast invertase Suc2 gene and established to be correctly targeted to the vacuole of transgenic tobacco cells (Sonnewald et al., The Plant J. 1:95–106 (1991)), the C-terminal vacuole targeting sequences of either tobacco chitinase A or in a separate experiment, the C-terminal sequence from barley lectin were fused to the secreted form of cucumber chitinase. The chimeric cucumber chitinase was correctly targeted to the vacuole of tobacco cells in both experiments (Neuhaus et al., Proc. Natl. Acad. Sci., 88:10362–10366 (1991); Bednarek and Raikhel, The Plant Cell, 3:1195–1206 (1991)). The source of the vacuole targeting sequence chosen to fuse operationally to the FTF protein is not critical so long as it is sufficient to accomplish the invention by correct targeting of a functional FTF protein to the vacuole of preferred transgenic plant cells.

Any 3' non-coding region capable of providing a polyadenylation signal and other regulatory sequences that may be required for the proper expression of the FTF coding region may be used to accomplish this invention. This would include the 3' end region from the nopaline synthase gene, the 3' end region from plant viral genes such as the 35S or 19S CaMV genes, from the 3' end region of the maize CI-gene or the 3' end sequences from any source such that the sequence employed provides the necessary information within its nucleic acid sequence to result in the proper expression of the promoter/FTF coding region combination to which it is operably linked. There are numerous examples in the art that teach the usefulness of different 3' non-coding regions (for example see Inglebrecht et al., Plant Cell, 1:671–680 (1989)).

By this description and the examples below, one skilled in the art could alter the chimeric constructs described by deleting the promoter, vacuole targeting sequence, coding sequence for the FTF gene or 31 transcriptional termination region and replace them with similar DNA fragments from microbial, plant, or other sources, resulting in a method and transgenic plants not unlike that which was described in this invention. The method described within may be applicable to a coding region from a microbial or plant source not necessarily with FTF activity, but any gene utilizing sucrose as a substrate to synthesize a carbohydrate polymer such as an alternansucrase, dextransucrase, glucosyltransferase or any sucrase.

Various methods of introducing (i.e., of transforming) a DNA sequence into higher plant cells are available to those skilled in the art (see EPO publications 0 295 959 A2 and 0 138 341 A1). Methods include transformation vectors based on Ti and Ri plasmids of Agrobacterium ssp. It is particularly preferred to use the binary-type of these vectors. Ti-derived vectors transform a variety of higher plants, such as tobacco, potato and canola.

For introduction into tobacco and potato the chimeric genes of this invention can be inserted into binary vectors as described in Example 1. The vectors are part of a binary Ti plasmid vector system (Bevan, Nuc. Acids Res., 12:8711–8720 (1984)), of *Agrobacterium tumefaciens*. For introduction into corn the chimeric genes of this invention will be transformed using high-velocity ballistic bombardment and metal particles coated with the nucleic acid constructs or fragments of the constructs sufficient to enable the invention (Klein et al., Nature (London), 327:70 (1987)); Klein, U.S. Pat. No. 4,945,050). Introduction of the DNA into plant cells is not of critical importance so long as the intent of the invention is carried out by transfer of the DNA or DNA fragment such that fructan polymers are synthesized and accumulated in a tissue and subcellular specific manner.

To assay for expression of the chimeric genes in leaves, seed or tuber of transformed plants, the FTF protein can be extracted, detected and quantified immunologically by methods known to those skilled in the art. Alternatively, leaves, seed or tuber tissue may be ground and extracted with a polar solution, isolating and concentrating large molecular weight polysaccharides (including fructans) which can then be detected by hydrolysis followed by quantitative enzymatic characterization or qualitative TLC analysis, combined with a kestose specific stain (wise et al., Anal. Chem., 27:33–36 (1955)).

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions. All publications including patents cited by Applicants herein are incorporated in their entirety by reference.

EXAMPLE 1

Characterization of SacB FTF Activity
Expression of the SacB FTF Gene in Bacillus The bacterial FTF (SacB) gene of this invention was obtained by screening a *Bacillus amyloliquefaciens* genomic DNA library with oligonucleotides based on the published sequence of the FTF gene, (Steinmetz et al., Mol. Gen. Genet., 200:220–228 (1985)). The cloning procedures were described in Tang et al., (Gene, 96:89–93 (1990); (Nagarajan et. al., U.S. Pat. No. 5,162,207). The source of DNA from which the FTF gene was isolated may be, for example, from any *Bacillus amyloliquefaciens*. These cells are available from the American Type Culture Collection, (Rockville, Md.). The coding sequence of the Bacillus FTF gene, was modified by addition of an EcoRV restriction enzyme recognition site at the 3' end of the 29 amino acid prokaryotic secretion signal cleavage site (beginning at bp 894). The EcoRV enzyme recognition site was added by site-directed mutagenesis, using a Muta-gene™ in vitro mutagenesis kit (Bio-Rad, Richmond, Calif.). The oligo nucleotide synthesized for use in the Muta-gene™ kit, containing the EcoRV site is listed as SEQ ID NO:1. The presence of the EcoRV site was determined by restriction enzyme analysis and later confirmed by DNA sequencing. The resulting plasmid, containing the modified FTF gene was designated pB311. The plasmid pB311 is useful for subsequent DNA manipulations, because it allows extraction of a DNA fragment containing the mature coding region of the FTF gene separate from the prokaryotic secretion signal.

Characterization of pB311 FTF Activity

Analysis of the modified FTF gene was accomplished first, by transforming *Bacillus subtillus* (strain BE1500) with pB311 plasmid DNA. This was performed by inoculating a 250 ml flask containing 10 mls of SPI media, with a *Bacillus subtillus* culture to an optical density at 600 nm of 0.15. The flask was incubated at 37° C. for three hours or until the optical density reached 1.0 at 600 nm. The cells were then diluted by adding 100 mls of SPII media and incubated at the same temperature for 90 minutes. The cells were precipitated from the media by centrifugation at 8000×g for 10 minutes at room temperature. Cells were resuspended in 10 mls of the supernatant (10 fold concentration). Cells treated in this way were transformed by placing 50 µl of SPII-EGTA into a sterile tube with 1–5 µg of plasmid DNA. 2 mls of SPII-EGTA was added to 1 ml of cells treated as described above and 300 µl of this mixture was added to the tube containing the plasmid DNA. This was incubated at 37° C. with gentle shaking for 20–30 minutes. Following incubation, 100 µl of LB media was added to the tube and incubation was continued at the same temperature for an additional 30 minutes. Aliquots (100 µl), of this solution were spread onto LB agar plates containing 5 µg/ml chloramphenicol for selection of cells containing the pB311 plasmid.

Tbase (1 X)
$(NH_4)_2SO_4$ 1 g
$K_2HPO_4$ 7 g
$KH_2PO_4$ 3 g
NaCitrate 0.5 g
$MgSO_4$ 0.1 g
ddwater to 500 ml SPI
to 100 ml of 1 X Tbase add the following,
1 ml 50% glucose
1 ml 10% yeast extract (DIFCO)
2 ml 1% casamino acids
1 ml 2% $MgSO_4$ SPII
This media is the same as SPI but also contains 0.5 ml of 0.1 M $CaCl_2$ SPII-EGTA
This media is the same as SPI but also contains 0.2 ml of 0.1 M EGTA.

LB Agar Plates
10 g tryptone (DIFCO)
5 g yeast extract
10 g sodium chloride
0.7% agar
ddwater to 1 L Preparation of Crude Bacterial Protein Extracts Crude extracts from Bacillus lines containing the plasmid pB311 were prepared by growing a 2 ml culture overnight, at 30° C. in nutrient (LB) media containing 5 µg/ml Chloramphenicol and 2% sucrose. Cells were removed from the media by centrifugation at 8000×g for 20 minutes. Soluble sugars were removed from the supernatant by adding 1 ml to a G-25M sephadex column (Pharmacia AB, Upsula Sweden) and centrifuging for 1 minute at 1500×g.

The solution containing secreted protein was concentrated 10-fold by volume using a Centricon-30 concentrator, (Amicon Co., Beverly, Mass.) as instructed by the manufacturer.

LB Media
- 10 g Tryptone (DIFCO)
- 5 g Yeast Extract
- 10 g NaCl
- ddwater to 1 L Assays for FTF Activity in Crude Protein Extracts FTF activity of was determined by several methods, including:

1) Glucose Oxidase Analysis of FTF Activity

FTF activity was assayed by incubation of protein extracts, at 37° C. for 30 minutes with a solution containing 2% sucrose in 50 mM potassium phosphate buffer (pH 6.0). This reaction was terminated by heating at 100° C. for 10 minutes. Negative controls were provided by heating the crude protein extract at 100° C. for 10 minutes before adding the phosphate buffered sucrose solution. FTF activity is destroyed by this treatment which allows the base-line, glucose concentration in the extract to be determined. FTF activity was determined by measuring glucose released from sucrose. This was accomplished by incubating the terminated reactions with glucose oxidase and peroxidase as described in a Glucose Trinder$^T$™ kit (Sigma Chemicals CO., St. Louis, Mo.), and determining the amount of quinoneimine dye formed by spectrophotometric analysis (O.D. measured at $340_{nm}$), in comparison to negative controls and glucose standards.

Assay of crude protein extracts from Bacillus containing the modified FTF protein using the glucose oxidase assay is represented in Table 1.

TABLE 1

| | (Optical Density at $A_{340}$) | |
|---|---|---|
| | (+) Sucrose | (−) Sucrose |
| No Extract | 0.18 | 0.18 |
| pB311 | 2.97 | 0.17 |
| pB311 (Heat inactivated) | 0.70 | 0.19 |

Data in Table 1 demonstrates that crude protein extracts from Bacillus containing the plasmid pB311, retains sucrose hydrolase activity.

2) Enzyme Linked Assay of FTF Activity

Crude protein extracts were incubated in a solution containing 2% sucrose and 50 mM potassium phosphate buffer (pH 6.0) at 37° C. for 30 minutes. Reactions were terminated by heating at 100° C. for 10 minutes. Negative controls, (inactivated protein) were provided by heating the crude protein extract to 100° C. for 10 minutes before adding the phosphate buffered sucrose solution. This treatment is sufficient for destroying enzyme activity and allows the contribution of glucose (base line activity) in the solution, independent of FTF activity, to be determined. FTF activity was measured by release of glucose from sucrose by incubating the terminated reactions with glucose assay mix at 30° C. for 20 minutes. This reaction was terminated by placing in a boiling water bath for 10 minutes and the activity was quantified by measuring conversion of NAD to NADH at 340 nm. Activity was compared to negative controls and glucose standards.

Additional information regarding FTF activity was obtained by measuring the amount of free fructose released from sucrose by incubating protein extracts with sucrose as described above. Activity is characterized in an enzyme linked reaction by incubating the terminated reactions in a solution containing hexose assay mix at 30° C. for 20 minutes and stopping the reaction by placing in a boiling water bath for 10 minutes. Phosphoglucose isomerase in this reaction converts free fructose to glucose, adding to the amount of NAD converted to NADH. The spectrophotometric reading at $340_{nm}$ represents both glucose and free fructose concentration. Comparison of spectrophotometric analysis of protein extracts incubated with glucose assay mix to those incubated with hexose assay mix allows determination of the level of free fructose in solution.

Glucose Assay Mix
- 0.2 M HEPES/NaOH (pH 8.0)
- 10 mM $MgCl_2$
- 2 mM NAD
- 2 mM ATP
- 10 mM DTT
- 2.5 units/ml Hexokinase
- 2.5 units/ml Glucose-6-phosphate dehydrogenase Hexose Assay Mix
- Glucose assay mix+4 units/ml Phophoglucose isomerase Data from enzyme linked analysis of Bacillus (containing the plasmid pB311), protein extracts is listed in Table 2.

TABLE 2

| | (Optical Density At $A_{340}$) | |
|---|---|---|
| | (+) Sucrose | (−) Sucrose |
| | Glucose Assay Mix | |
| No Extract | 0.09 | 0.10 |
| pB311-(heat inactivated) | 0.07 | 0.09 |
| pB311 | 1.17 | 0.36 |
| | Hexose Assay Mix | |
| No Extract | 0.10 | 0.18 |
| pB311 | 1.21 | 0.33 |

The data in Table 2 confirms the results of the glucose oxidase assay, (see Table 1 above) that the EcoRV modified FTF protein retains sucrose hydrolysis activity. Table 2 also demonstrates that fructose is not present in a 1:1 ratio, as would be expected if hydrolysis of sucrose was the only activity present in crude protein extracts. Polymerized fructose does not react with phosphoglucose isomerase in the hexose assay mix. Therefore, the lower level of free fructose suggests that not only does the protein in crude extracts utilize sucrose, releasing glucose, but also sequesters fructose, most likely by polymerization.

3) Assay of FTF Activity by HPLC

Qualitative analysis of FTF activity was performed by establishing the presence of large molecular weight carbohydrate polymers formed subsequent to incubation of crude protein extracts in a solution of 2% sucrose and 50 mM potassium phosphate buffer (pH 6.0) at 37° C. for 30 minutes to 1 hour. Negative controls were provided by heating the crude protein extract to 100° C. for 10 minutes before adding the phosphate buffered sucrose solution. Following incubation, the fructan produced was analyzed by High Performance Anion Exchange Chromatography, using a 0–100 mM NaOH gradient on a Dionex PA-100 column and Dionex PAD detector (Dionex Sunnyvale, Calif.). The chromatographic profiles of the reactions were compared to those obtained using authentic levan standards (Sigma Chemicals CO., St. Louis, Mo.).

4) Assay for Fructose Polymers by Thin Layer Chromatography

Qualitative analysis of FTF activity was also performed by incubation of crude protein extracts in a solution containing 2% sucrose and 50 mM potassium phosphate buffer (pH 6.0) at 37° C. for 30 minutes to 1 hour. Negative controls were provided by heating the crude protein extract to 100° C. for 10 minutes before adding the phosphate buffered sucrose solution. After incubation, 5–10 μl of the reaction was spotted on a 20 cm×20 cm Fisher Redi/plate™ (Fisher Scientific, Pittsburg, Pa.) along with positive controls (i.e., fructose, glucose, sucrose, starch and chicory inulin purchased from Sigma Chemicals CO., St. Louis, Mo.). The plate was run in a TLC chamber containing a solvent system of water, n-butanol, and 2-propanol in a ratio of 4:3:12. When the solvent front reached to within 1 cm of the top, the plate was removed from the chamber and air dried. The plate was then sprayed with a kestose specific stain (Wise et al., Anal. Chem., 27:33–36 (1955)). The stain is made by diluting phosphoric acid to 1 M in water saturated n-butanol. To this was added 3 g of urea followed by 5 ml of ethyl alcohol.

The kestose specific stain was allowed to air dry on the TLC plate. Fructose and fructose polymers produced from sucrose by the action of FTF were visualized by placing the TLC plate at 100° C. for 5–10 minutes. Glucose produced very faint signals in this assay and starch produced no detectable signal. Fructose and sucrose signals ran near the solvent front and inulin standards produced signals that did not migrate significantly from the origin.

5) Quantification of Fructan by Anthrone Analysis

Extracts were processed by grinding in 80% ethanol and incubated at 70° C. for 10–15 minutes. Ethanol insoluble material was precipitated by centrifugation (13000×g), for 5 minutes. The pellet was resuspended in 80% ethanol, heated to 70° C. for 10–15 minutes and pelleted, once again. This step was repeated a third time and the final pellet was resuspended in water. The solution was incubated at 70° C. for 10–20 minutes and centrifuged for 5 minutes at 13000×g. The supernatant removed was used for determination of fructan concentration.

Fructan concentration was determined by incubating ethanol insoluble extracts at 100° C. with concentrated HCl for 10 minutes. This was cooled and then neutralized with NaOH. The HCl treated samples were added to 1 ml anthrone solution at 40° C. for 20 minutes, cooled and the amount of fructose was determined by specrophotometric analysis at $A_{620}$ in comparison to known fructose standards. Because the fraction assayed by anthrone was ethanol insoluble, the carbohydrate in its original state, was considered to be of large molecular weight (i.e., fructan). Soluble carbohydrate that could contribute to the spectrophotometric reading was removed by the steps involving incubation in hot 80% ethanol. The extracts were determined to be free of soluble carbohydrate that would interfere with accurate estimates by TLC analysis. Therefore, anthrone analysis, as described, provides a reasonable estimate of the amount of fructan present.

Anthrone Solution 86 mls of concentrated sulfuric acid was added to 20 mls of water. To this was added 0.15 g anthrone (Sigma Chemicals, St. Louis, Mo.).

EXAMPLE 2

Chimeric Gene Constructs for Expression of the SacB FTF Gene in *Nicotiana tabacum*

Constitutive Expression of a FTF in *Nicotiana tabacum*

A cassette designed for constitutive, cytosolic expression of the Bacillus FTF gene throughout leaves and stems of *Nicotiana tabacum* was constructed by first adding an NcoI site at the initiation codon of the SSU gene, to facilitate subcloning DNA fragments. This was accomplished by digesting the plasmid pNtSS23 (Mazur and Chui, Nuc. Acids Res., 13:2373–2386 (1985), with SphI and deleting the 3' overhang nucleotides by incubation with *E. coli* DNA polymerase in a solution containing 40 mM potassium phosphate, (pH 7.5), 6.6 mM magnesium chloride and 1 mM 2-mercaptoethanol, at 37° C. for 10 minutes. An NcoI linker (New England Biolabs) was ligated and the plasmid sequenced to determine that the ATG of the new NcoI site was in the same position as the original initiation codon. This plasmid was designated p338.

A 1.0 Kb HindIII-NcoI fragment from plasmid p338 was blunt-end filled by standard procedures using dNTPs and Klenow enzyme. The sequence of the HindIII-NcoI fragment contains the SSU regulatory sequences necessary for light induced gene expression in stem and leaves of dicotyledonous plants (Mazur and Chui, Nuc. Acids Res. 13:2373–2386, (1985)). This fragment was ligated into pDH51 (Pietrzak et al., Nuc. Acids Res., 14:5857–5868 (1986)) which had been previously digested with EcoRI and blunt-end filled, then digested with SmaI, replacing the CaMV 35S promoter. The ligation mixes were transformed into *E. coli* strain DH5a [supE44 del lacU169 (phi 80 lacZ del M15) hsdR17 recA1 endA1 gyr196 thi1 relA1] and ampicillin-resistant colonies selected. The clones were screened by restriction endonuclease digestion analyses of isolated plasmid DNAs.

The NcoI site, at the initiation codon in the resulting plasmid, called pSSUDH51, was reconstituted and an EcoRV site, was also added, in frame with the initiation codon, by a PCR reaction using oligonucleotides, synthesized on an Applied Biosystems synthesizer. Oligonucleotides used as primers are listed as SEQ ID NO:2 and SEQ ID NO:3. SEQ ID NO:3 also contains an XbaI site for subcloning purposes.

PCR reaction mixtures included 0.1–0.3 ng of each primer, up to 1 μg of template DNA, 4 μl of 2.5 mM dNTPS, 5 μl of 10×reaction buffer (800 mM Tris (pH 9.0), 200 mM $(NH_4)_2SO_4$, 15 mM $MgCl_2$), 1 μl Perfect Match™ (Stratagene, La Jolla, Calif.) and $H_2O$ to a final volume of 49 μl. After an initial denaturation at 95° C. for 5 mins, 1 μl of TAQ™ polymerase was added to each reaction and the following cycle program was run: 1 minute at 95° C., 2 minutes at 42° C. and 3 minutes at 72° C. for 40 cycles. PCR generated DNA fragments were separated on 1.2% agarose gels and visualized with ethidium bromide.

The isolated PCR fragment was digested with BglII and XbaI and ligated into pSSUDH51, also digested with the same restriction enzymes, resulting in the plasmid pSSU/P. The coding sequence for the *Bacillus amyloliquefaciens* FTF gene, without the bacterial secretion signal was added to pSSU/P by digesting pB311 with EcoRV and XbaI. A 1.3 Kb fragment containing the mature FTF coding region was ligated into pSSU/P also digested with EcoRV and XbaI, resulting in the plasmid pSSU-SacB. The SSU promoter, beginning at base pair 365 (BglII site, see Mazur and Chui, Nuc. Acid Res., 13:2373–2386 (1985), the complete coding sequence for the FTF gene and the CaMV transcription termination sequence was isolated from pSSU-SacB by digesting with BglII-KpnI and recovering the DNA fragment which was inserted into an *Agrobacterium tumefaciens* binary Ti plasmid based vector pZS97.

The binary vectors pZS97 or pZS97K were used to transfer the chimeric genes to plants. Both binary vectors pZS97 and pZS97K are part of a binary Ti plasmid vector system (Bevan, Nucl. Acids. Res. 12:8711–8720 (1984)) of *Agrobacterium tumefaciens*. The vectors contain: (1) the chimeric gene nopaline synthase::neomycin phosphotransferase (nos::NPTII) as a selectable marker for transformed plant cells (Bevan et al., Nature 304:184–186 (1983)], (2) the left and right borders of the T-DNA of the Ti plasmid [Bevan, Nucl. Acids. Res. 12:8711–8720 (1984)), (3) the *E. coli* lacZ α-complementing segment [Viering et al., Gene 19:259–267 (1982)) with unique SalI, BamHI, and KpnI sites (pSK97K) or unique HindIII, BamHI, and KpnI sites (pZS97) in the polylinker region, (4) the bacterial replication origin from the Pseudomonas plasmid pVS1 (Itoh et al., Plasmid 11:206–220 (1984)), and (5) the bacterial neomycin phosphotransferase gene from Tn5 (Berg et al., Proc. Natl. Acad. Sci. U.S.A. 72:3628–3632 (1975)) (pZS97K) or the bacterial β-lactamase gene (pZS97) as selectable markers for transformed Agrobacterium. Binary vectors containing the chimeric genes were transferred by tri-parental mating (Ruvkin et al., Nature 289:85–88 (1981)) to Agrobacterium strain LBA4404/pAL4404 (Hockema et al., Nature 303:179–180 (1983)) and selected for ampicillin resistance (pZS97) or kanamycin resistance (pZS97K).

Transformation of Tobacco Leaf Disk by Infection with Agrobacterium

Cultures of Agrobacterium containing the binary vector were used to transform tobacco leaf disks (Horsch et al., Science 227:1229–1231 (1985). Leaves were sterilized by a 30 minute wash in 900 ml sterile water, 100 ml Chlorox bleach and 10 ml of 10% SDS. Leaves were rinsed three times in sterile water and disks were prepared by cutting into 1 cm squares or punched with a sterile hole punch. Disks were inoculated with Agrobacterium containing appropriate binary vectors by submerging the leaf pieces into LB media containing the bacteria. The inoculated disks were transferred to CN media, incubated in the light at room temperature for three days. After the three day incubation the leaf disks were transferred to CN media containing 500 mg/L Claforan (cefotaxime) and 300 mg/L kanamycin and incubated for an additional 4–6 weeks. At this time shoots that develop are excised from the disks and placed in rooting media containing 500 mg/L Claforan (cefotaxime) and 300 mg/L kanamycin. Roots develop on approximately 40–50% of the shoots after 2–4 weeks on this media. The rooted shoots are transplanted to wet metro-mix in an 8" pot and assayed for the presence of the transferred gene.

CN Media

One package of Murashige and Skoog (MS) minimal organic medium with sucrose (KC biochemicals or GIBCO)

1% BAP 0.1 μg/L Naladixic acid 4 g agar 500 ml water (pH 5.8)

Rooting Media

One package of Murashige and Skoog (MS) minimal organic medium without sucrose (KC biochemicals or GIBCO)

10 g sucrose 4 g agar 500 ml water (pH 5.8)

Expression of pSSU-SacB Prevents Regeneration of Tobacco

Cultures of Agrobacterium containing the binary vector, capable of transferring the pSSU-SacB expression cassette into the genome of tobacco were used to inoculate tobacco leaf disks by co-cultivation (see above and Horsch et al., Science 227:1229–1231 (1985)). Attempts to regenerate transgenic plants in selective medium containing kanamycin resulted in only 3 viable shoots. The shoots were excised and placed on rooting media however, roots did not form after more than ample time to do so (3–5 weeks). Control leaf disks incubated with *Agrobacterium tumefaciens* containing only the binary vector pZS97 produced at least 10 times more shoots using the same number of inoculated leaf disks. Control shoots formed roots on rooting media containing kanamycin within 2–4 weeks. This complete experiment, beginning with the subcloning of the of the FTF gene fragment from pB311 described above, through the transfer to the binary vector, tri-parental mating and incubation with tobacco leaf disks was carried out a second time in an attempt to regenerate viable tobacco plants containing the SSU-SacB expression cassette. The second experiment resulted in only 4 regenerated tobacco shoots on selective media.

Testing for Potential Transformants for Kanamycin Resistance by Cultivation on Callus Media Sterile leaf disks from the 4 regenerated shoots described above and positive control tissue (transformed with only a binary vector), were placed on callus media containing 50 μg/ml kanamycin for selection. Callus formed around the edges of positive control leaf disks carrying only the NPT II gene after 4–6 weeks incubation at room temperature. Callus tissue did not form on the disks taken from the 4 shoots obtained in the experiment described above. It appears likely that the shoots formed in this experiment were not true transformants, but "escapes" from the kanamycin selection in CN media. The results obtained from these two experiments indicate that expression of the FTF gene in tobacco cells with this promoter is extremely detrimental to the growth, development and regeneration of tobacco plants.

Callus Media

One package of Murashige and Skoog (MS) minimal organic media (KC Biologicals)

10 g sucrose 4 g agar water up to 500 mls (pH 5.8)

EXAMPLE 3

Inducible Expression of the Bacterial FTF in Tobacco

Construction of an Inducible FTF Expression Cassette

Attempts to understand the detrimental nature of FTF activity, when expressed in the cytosol of a tobacco leaf cell was possible by constructing an inducible expression cassette. Transforming tobacco with an FTF gene that is not transcribed into mRNA, and therefore, translated into functional protein until induced, allows regeneration without concern for inhibition of growth and development by FTF activity in the cell. The gene can subsequently be activated for analysis of the effect on various stages of tobacco development.

Construction of a Chemically Induced FTF Expression Cassette

The SacB promoter and coding region, including the bacterial secretion signal, was removed from plasmid pB311 (Tang et al., Gene 96:89–93 (1990); Nagarajan et al. U.S.

Pat. No. 5,162,207) by cutting with the restriction enzymes KpnI and XbaI. The KpnI-XbaI fragment was ligated into pUC18 (New England Biolabs. Beverly, Mass.), cut with the same restriction enzymes. The resulting plasmid was called p3114. The plasmid p3114 was then digested with EcoRV and HincII, and the mature FTF coding regions was isolated from the promoter and secretion signal on a 1.3 Kb DNA fragment. The 1.3 Kb fragment was inserted into a Bluescript SK(+) cloning vector (Stratagene, La Jolla, Calif.), digested with EcoRV and SmaI. A BglII linker was added at the XhoI site, in Bluescript SK(+) plasmid containing the EcoRV-HincII fragment of p3114, approximately 48 bases 3' of the translation termination signal. The resulting plasmid was designated SacB-BglII. A transcription termination region was added to SacB-BglII by ligating a 503 bp BglII/KpnI fragment from the 2-1.12 gene (Hershey and Stoner, Plant Mol. Biol. 17:679–690 (1991); Hershey, U.S. Pat. No. 7,327,205) into the plasmid digested with the same restriction enzymes. The resulting plasmid, containing the mature coding region of the SacB FTF gene and the 2-1.12 transcription termination region was designated SacB:2-1.

An inducible expression cassette was constructed, consisting of a 2-2.3 promoter region (Hershey and Stoner, Plant Mol. Biol., 17:679–690 (1991)), the translation leader from the chlorophyll a/b binding protein (Cab) gene, (Dunsmuir, Nuc. Acids Res., 13:2503–2518 (1985)), and the 3' transcription termination region from the nopaline synthase (Nos) gene (Depicker et al., J. Mol. Appl. Genet., 1:561–570 (1982)). The initiation codon (ATG), is located within a NcoI restriction enzyme site (added by NcoI linker ligation) at the junction of the 2-1.3 promoter and the Cab translation leader. The inducible vector was designated TDS136.

The plasmid TDS136 was digesting with NcoI and the 5' overhang filled with dNTPs and klenow enzyme. The NcoI blunted plasmid was then digested with BamHI and a 1.0 Kb fragment containing the 2-2.3 promoter was isolated. This fragment was ligated into SacB:2-1 digested with BamHI and EcoRV. The resulting plasmid, CIP:SacB:2-1 contained the initiation codon (ATG) in frame with the mature FTF coding sequence and a 2-1 3' region. This plasmid was digested with BamHI and KpnI, a 2.8 Kb fragment was isolated and ligated into the binary plasmid pZS97K. The binary vector containing the promoter and transcription termination sequences, functionally linked to the FTF gene was placed into Agrobacterium by tri-parental mating using techniques, described in Example 2. The binary vector containing the inducible expression vector was introduced into tobacco by the transformation methods also described in Example 2.

Extraction of DNA from Tobacco Leaves

Leaves from regenerated tobacco plants were used to prepare DNA extracts. The extracts were used for PCR analysis to confirm whether a tobacco line contained the CIP:SacB:2-1 expression cassette. Two grams of leaf tissue, derived from leaves 10 cm in length were placed into a mortar containing liquid nitrogen on dry ice. The tissue was ground to a fine powder. This powder was added to 10 ml of extraction buffer (50 mM Tris (pH 9.0), 10 mM EDTA, 2% SDS) at 50° C. in a sterile 50 ml polyethylene centrifuge tube. Five milligrams of proteinase K was added and the mixture incubated at 50° C. for 10 minutes with occasional mixing. The solution was extracted twice with phenol:chloroform:isoamyl alcohol [25:24:1] and twice with chloroform:isoamyl alcohol [24:1]. The aqueous layer was brought to 0.3 M sodium acetate and precipitated with 2.5 volumes of cold ethanol. The solution was centrifuged at 8000×g, the pellet, containing the nucleic acids was washed with 70% ethanol and vacuum dried. Pellets were resuspended in 10.0 ml of water, mixed with an equal volume of 4 M $LiCl_2$ and allowed to precipitate on ice for one hour. The solution was then centrifuged at 12,000×g for 25 minutes at 4° C. RNA is pelleted in this step and DNA remains in solution. The supernatant containing the DNA was precipitated with 1 volume of cold 2-propanol, collected by centrifugation, washed with 70% ethanol and resuspended in water, for use in PCR analyses.

Successful transformation was determined by PCR reaction (methods described in Example 2), using DNA isolated from leaves as the template and the PCR primers listed as SEQ ID NO:4 and SEQ ID NO:5. The primers are specific for regions of the FTF gene about 1.3 Kb apart. Only those plants producing the expected 1.3 Kb PCR DNA fragment were designated as positive for the transgene.

Induction of the In2-2 Promoter and Chimeric Genes in Transgenic Plants

Induction of the CIP:SacB:In2-1 expression vector was accomplished by cutting a transgenic tobacco leaf and immediately submerging the stem end in 0.5×Hoagland's solution (KC Biologicals) containing 200 mg/l of N-(aminocarbonyl)-2-chlorobenzenesulfonamide (2-CBSU). Induction of RNA occurs in leaf tissue after 1–2 hours with maximal induction occurring after 24 hours following the initial treatment (Hershey and Stoner, Plant Mol. Biol., 17:679–690 (1991)). Control tissue was obtained by immersion of transgenic leaves in 0.5×Hoagland's solution without addition of 2-CBSU.

Analysis of 2-CBSU Induced FTF Expression in Transgenic Tobacco Leaves

Following a 6–8 hour induction, the transformed leaves developed a water-logged phenotype and were noticeably wilted. A longer induction (12–14 hours), resulted in complete destruction of transformed leaves. Thin sections of transformed leaves induced for 6–8 hours (sliced thinly with a razor), and viewed under a light microscope, demonstrated that the internal structure of the cell had collapsed. The chloroplasts no longer retained organization, but instead had condensed into the center of the cell, normally occupied by the vacuole. Control leaves (uninduced, tobacco containing the CIP:SacB:In2-1 expression vector) remained rigid and green even through the 12–14 hour induction.

Isolation of Fructan from Transgenic Plant Tissue

Isolation of fructan from CIP:SacB:In2-1 transformed leaves, induced for 12–14 hours was accomplished by extraction and separation of soluble and insoluble carbohydrates. Tissue, (200–400 mg) from transgenic leaves was ground in 500 μl of 80% ethanol in a microfuge tube with a plastic pestle and heated to 80° C. for 10 minutes. The heated mixture was centrifuged at 10000×g for 10–15 minutes, room temperature. The supernatant was discarded and the pellet resuspended in 500 μl of 80% ethanol, mixed thoroughly, heated at 80° C. for 10 minutes and centrifuged. This step was repeated a third time and the final pellet was resuspended in 200–400 μl of sterile water. The solution was mixed thoroughly and heated to 100° C. for 10–20 minutes and centrifuged at 10000×g for 10 minutes. The supernatant from this centrifugation step contains large molecular carbohydrate including fructans and is essentially free of soluble sugars. Detection of fructans in the supernatant may be accomplished by any one of several methods listed in Example 1. Detection of fructan accumulated in transgenic tissue in this experiment was accomplished the enzyme linked assay, described in Example 1. Addition of concentrated HCl to the final supernatant and incubation at 70° C. for 10 minutes, followed by neutralization with NaOH is sufficient to completely hydrolyze any fructan present into individual fructose residues. The concentration of fructose after this treatment is compared to known fructose standards and to wild-type control extracts which do not contain fructan.

The result of analysis from CIP:SacB:In2-1 induced leaves was positive for fructan, the level of free fructose in the treated supernatant was higher than that found in wild-type controls. The results suggest that FTF activity and fructan accumulation brought about destruction of 2-CBSU induced leaves. The experimental data listed above and that of Example 2, demonstrate that a constituatively expressed, cytosolic FTF is deleterious to normal cell function. Destruction of tobacco leaves containing the CIP:SacB:In2-1 cassette, only when induced, clearly implicates the activity of this protein as the cause of the lethal effects, when expressed in the cytosol of a plant cell.

The evidence strongly suggests that enzymes with activity such the Bacillus FTF gene or similar genes with sucrose metabolic activity expressed cytosolically, interfere with sucrose synthesis, transport of sucrose to sink tissue and/or alter osmotic potential in the cell. The result is serious detrimental effect to plant cells and therefore, based on this data, it must be concluded that successful transformation of plants with a protein possessing FTF or similar activity, must take into account proper tissue specific or subcellular regulatory signals.

EXAMPLE 4

Expression of the Bacillus FTF Gene in the Vacuole of a Plant Cell

Constitutive expression of the bacterial FTF gene in the cytosol of a leaf cell was not successful. This, together with the knowledge that fructans synthesized in plants such as Jerusalem Artichoke and Chicory, accumulate in the vacuole of storage cells, suggested that targeting FTF to the vacuole, utilizing sucrose in that compartment, would lead to accumulation of fructan in a transgenic plant cell without significant deleterious effect.

Construction of Chemically Induced, Vacuole Targeted FTF Expression Cassette
Addition of the Dicotyledenous Sweet Potato Sporamin Vacuole Targeting Sequence to FTF A sporamin vacuole targeting based on the published DNA sequence, (Matsuoka et al., J. Biol. Chem., 32:19750–19757 (1990)) was synthesized as two separate oligonucleotides. The oligonucleotides SEQ ID NO:6 and SEQ ID NO:7 contain coding information for the 37 amino acid prepro- and pro-peptide that is sufficient for targeting operably linked, chimeric proteins to the vacuole of transgenic plant cells. The amino acid sequence coded for by the oligonucleotides is listed as SEQ ID NO:8.

The oligonucleotides SEQ ID NO:6 and SEQ ID NO:7 also contain the restriction enzyme recognition sites for SpeI, BspHI, NcoI, and XhoI, useful in subcloning fragments into functional expression cassettes. Oligonucleotides coding for the sporamin target sequence were phosphorylated in a reaction containing 50 mm Tris-HCL (pH 7.5), 7 mM MgCl, 10 mM 2-mercaptoethanol, 1 pmole 5'-termini and 1 unit T4 Polynucleotide Kinase in 25 μl, incubated at 37° C. for 30 minutes. The phosphorylated oligonucleotides were precipitated in 2 volumes of ethanol by centifugation at 10000×g for 20 minutes and resuspended in water. Following resuspension, 250 ng of each oligo was mixed, heated to 100° C. for 5 minutes and allowed to anneal by cooling at room temperature for 30 minutes.

Annealed oligonucleotides were digested and ligated into Bluescript SK(+), previously cut with the restriction enzymes SpeI and XhoI. The sequence was verified by di-deoxy chain termination sequencing and compared to that described in Matsuoka et al., J. Biol. Chem., 32:19750–19757 (1990). The sporamin target sequence was then isolated from the Bluescript SK(+) cloning vector by a BspHI and XhoI digest and ligated into TDS-136, (previously digested with NcoI and XhoI). The resulting plasmid 136-Spor contained a chemically induced promoter region (2-2) and the sporamin vacuole targeting sequence functionally linked so that the targeting sequence would be translated from the native CIP initiation codon. The 136-Spor plasmid was then digested with NcoI, blunt end filled with klenow enzyme, and further digested with XbaI. A 1.1 Kb fragment containing the CI-promoter and vacuole targeting sequence was isolated and ligated to SacB:In 2-1 which was previously digested with XbaI and EcoRV. This resulted in a complete expression cassette containing the CI-promoter functionally linked to the sporamin vacuole targeting sequence, which was functionally linked to the Bacillus FTF gene and the In 2-1 transcription termination sequence. The plasmid called CIP-Spor-SacB was digested with BamHI and KpnI. The FTF gene and suitable regulatory and targeting sequences were isolated on a single DNA fragment and ligated into the binary vector pZS97K, cut with the same restriction enzymes. Mobilization of the expression cassette into Agrobacterium by tri-parental mating and transformation into tobacco were described in Example 2. Assay for the presence of the CIP-Spor-SacB expression cassette in transformed tobacco lines was by PCR analysis (Example 2), using the primers specific for the FTF gene, described in Example 3 (SEQ ID NO:4 and 5).
Induction of the CIP-Spor-SacB Expression Cassette in Tobacco Fully expanded mature leaves and immature, 8–10 cm leaves from PCR positive tobacco plants containing the CIP-Spor-SacB cassette were induced by methods described in Example 3. Induction of the CIP:SacB:In2-1 cassette (Untargeted FTF, Example 3), resulted in significant damage to tobacco leaves in a very short period. The addition of a functional vacuole targeting sequence in this experiment had a significant effect on the phenotype of the leaves induced by 2-CBSU for an equivalent amount of time. Eight to ten hour induction of CIP-Spor-SacB (vacuole targeted FTF), containing tobacco leaves displayed no phenotypic differences compared to positive control (wild-type tobacco) leaves. Negative control leaves, without a vacuole targeting signal (CIP:SacB:In2-1), once again appeared water logged and began to wilt. The CIP-Spor-SacB tobacco lines eventually demonstrated a wilting phenotype, but only after 24–36 hours of induction. The wild-type control leaves also demonstrated a slightly wilted phenotype, after 36 hours of induction however, the CIP:SacB:In2-1 leaves were brown, dry and completely destroyed at this time point.
Isolation of Total Cellular RNA from Induced Leaf Tissue CIP-Spor-SacB and wild-type control leaves, induced for 12–14 hours were removed from the Hoagland's solution containing 2-CBSU or from the Hoagland's alone, and rinsed in sterile water. Isolation of total RNA from induced and uninduced leaves was with guanidine thiocyanate reagent.

Guanidine thiocyanate reagent was prepared by dissolving the contents of a 100 g bottle (Kodak Laboratory and Specialty Chemicals) in 80 ml of water and adding 10.6 ml of 1 M Tris-HCL, (pH 7.6) and 10.6 ml of 200 mM $Na_2$ EDTA. The solution was stirred until the contents of the bottle was dissolved and 4.24 g of sodium lauryl sarcosinate and 2.1 ml 2-mercaptoethanol were added. The volume of solution was adjusted to 212 ml with sterile water and stored at 4° C. in the dark until used.

Leaf samples were quick-frozen by immersion in liquid nitrogen. Once cooled, 10–15 g of tissue was transferred to a mortar and ground to a fine powder. The powdered tissue was then placed in a 150 ml Corex™ centrifuge bottle containing five volumes (v/w) of ice cold guanidine thiocyanate reagent, 0.5 ml of chloroform, 0.2 ml n-octanol, and 2.5 ml vanadyl ribonucleoside complex (Bethesda Research Laboratories, Gaithersburg, Md.). The tissue was further ground in a Brinkman polytron PT-10/35 at maximum speed for 1 minute. The crude tissue extract was then centrifuged at 27,000×g for 10 minutes at 4° C. The supernatant was decanted into a graduated cylinder and 1 g of CsCl was added for each 2.5 ml of solution. The mixture was centrifuged at 36,000×g for 10 minutes at 4° C. and the resulting supernatant was layered over 2 ml pads of 5.7 M CsCl in a $9/16"\times3\frac{1}{2}"$ polyallomar ultracentrifuge tube. The step gradient was centrifuged at 28,000×g for 15–20 hours at 10° C. using a Beckman SW41Ti rotor. Following centrifugation the tubes were carefully drained and the sides wiped clean. The pellets were dissolved in 0.2 ml TES buffer (10 mM TRIS-HCL (pH 7.4), 5 mM EDTA and 1% SDS) and transferred to a 15 ml centrifuge tube. The RNA was combined with an equal volume of chloroform:n-butanol (4:1) and vortexed briefly. The resulting emulsion was centrifuged at 8,000×g for 5 minutes at 20° C. The aqueous layer was transferred to a fresh 15 ml centrifuge tube, the organic phase was back extracted with an equal volume of TES and pooled with the previous aqueous layer. RNA was precipitated at −20° C. for at least 2 hours after adding a tenth volume of 3.0 M sodium acetate (pH 6.0) and two volumes of ethanol. The RNA was recovered by centrifugation at 10,000×g for 20 minutes at 4° C. The supernatant layer was carefully aspirated off and the RNA was dissolved in 0.5 ml of sterile water. A small aliquot was diluted 100 fold with water and the $A_{260}$ of this dilution was measured to determine RNA concentration.

Slot Blot Analysis of Total RNA

A nitrocellulose filter (Schleicher and Schuell BA-85) was wetted by soaking it twice for 10 minutes in water, followed by a 10 minute soak in 1 M ammonium acetate. The filter was then placed in a slot blot apparatus (Schleicher and Schuell, Kheene, N.H.). Multiple 2.5 μg samples of RNA from untreated leaves and from leaves induced with 2-CBSU were diluted to a final volume of 80 μl with sterile water. Following the dilution, 40 μl of denaturation buffer (30% formaldehyde, 100 mM sodium phosphate (pH 6.8) was added to each sample and all samples were then incubated at 65° C. for 10–20 minutes and quick-cooled in an ice slurry for 5 minutes. After cooling, 30 μl of 4 M ammonium acetate was added to each sample and 150 μl samples were added to slots in the blotting cell with the aid of a 10–15 mm Hg vacuum. The filter was removed from the blotting cell, air dried and baked for 2 hours at 70° C. in vacuo. The filter was incubated in 10 mls of prehybridization buffer (50% deionized formamide, 5×SSC, 5×Denhardt's, 100 μg/ml denatured calf thymus DNA, 40 mM sodium phosphate (pH 6.8) and 0.5% bovine serum albumin) in a heat sealable bag for 6 hours at 42° C. with occasional mixing. The filter was hybridized with a nick-translated (labeled with $^{32}P$ in a BRL nick-translation kit), FTF gene probe (a 1.3 Kb, EcoRV-XbaI DNA fragment, isolated from the plasmid pB311 and homologous to only the FTF coding region). This was performed by discarding the prehybridization solution from the bag and replacing it with 2.5 mls of hybridization buffer (50% deionized formamide, 5×SSC, 100 μg/ml denature calf thymus DNA and 40 mM sodium phosphate, (pH 6.8)) containing $1.25\times10^7$ cpm of nick-translated FTF gene probe described above. Nick-translated DNA was denatured by boiling for 10 minutes followed by quick-cooling on ice. The filter was then hybridized overnight at 42° C. with occasional mixing.

The filter, removed from the bag the next day was washed twice at room temperature for 10–15 minutes on a rocking shaker in 2×SSC, 1 mM EDTA, 20 mM sodium phosphate (pH 6.8), 1 mM sodium pyrophosphate, and 0.5% SDS. This was followed by two washes for 30 minutes at 65° C. with 0.1×SSC and 0.5% SDS. The filter was briefly air dried, wrapped in polystyrene food wrap and subjected to autoradiography overnight using Kodak XAR-5 film and a single DuPont Lightning Plus intensifying screen.

Wild-type tobacco produced no signal on X-ray film exposed to the slot blot filter for up to 48 hours. However, 15 of the 22 transgenic CIP-Spor-SacB lines contained RNA which hybridized specifically to the FTF gene probe producing a positive signal on X-ray film only in lanes containing RNA from induced leaves. The amount of RNA induced varied greatly among lines.

Targeting FTF to the Vacuole of Tobacco Cells Through the Use of a Monocotyledenous Barley Lectin Vacuole Targeting Sequence Construction of CIP-Blec-SacB An expression cassette containing the FTF gene functionally fused to the N and C-terminal Barley lectin ER and vacuole targeting sequences, linked to chemically induced regulatory signals was constructed by first synthesizing two complimentary oligonucleotides, listed as SEQ ID NO:9 and SEQ ID NO:10. The oligonucleotides, SEQ ID NO:9 and SEQ ID NO:10 are based on published DNA sequence demonstrated to be necessary and sufficient for targeting foreign proteins which have entered the secretory system to the vacuole in tobacco as described in Bednarek et al., (Plant Cell, 2:1145–1155 (1990); Dombrowski et al., Plant Cell, 5:587–596 (1993)). The oligonucleotides were phosphorylated and annealed as described above. The annealed oligonucleotides were digested with BglII and HincII (restriction enzyme sites contained in the oligonucleotide DNA sequences), and ligated to the plasmid SacB:In2-1 which had been previously digested with the same restriction enzymes. This resulted in the plasmid SacB:CTPP:In2-1.

The C-terminal vacuole targeting sequence of barley lectin, (contained in SEQ ID NO:9 and SEQ ID NO:10) is sufficient to direct a protein into the vacuole of a plant cell only after it has entered the secretory system. The amino acid sequence of the C-terminal barley lectin gene, coded for by the oligonucleotides is listed in SEQ ID NO:11. The barley lectin protein also contains an N-terminal signal for directing proteins into the secretory system. The N-terminal secretory signal was cloned from barley DNA by a PCR reaction.

Two oligonucleotides primers which flank each end of the barley lectin secretory signal were synthesized and used in a PCR reaction. The nucleotide sequence of the 5' primer is listed in SEQ ID NO:12 and the nucleotide sequence of the reverse compliment 3' primer is listed as SEQ ID NO:13. The oligonucleotides of SEQ ID NO:12 also contain the sequence recognition site for the restriction enzymes EcoRI and BspHI. The oligonucleotide primer SEQ ID NO:13, contains the sequence corresponding to the recognition site for the restriction enzymes NcoI and SalI. The primers, (SEQ ID NO:12 and SEQ ID NO:13) are based on the published N-terminal secretory (ER) signal of the Barley lectin gene (Lerner and Raikel, Plant Phys., 91:124–129 (1989)). The oligonucleotides were annealed to Barley genomic DNA, used as the template and run in a PCR reaction (by methods described in Example 2). A DNA fragment of approximately 100 bp was recovered from the PCR reaction, digested with EcoRI and SalI and ligated into the cloning vector, Bluescript SK(+) (Stratagene, La Jolla, Calif.). The resulting clone was designated SK-5' BLEC. The inserted DNA fragment was sequenced to confirm that the nucleotides were identical to the published sequence for the Barley 5' ER signal.

The 5' Barley ER signal was operably fused at the initiation codon of the CI-promoter by digesting SK-5'Blec with BspHI and SalI. The PCR fragment was ligated into TDS-136, previously digested with NcoI and SalI, resulting in plasmid 136-BLEC. CIP:Blec:SacB:Blec:In2-1 was completed by digesting 136-Blec with NcoI and blunt end filling with Klenow enzyme, followed by precipitating the DNA and digestion with the restriction enzyme XbaI. The isolated DNA fragment containing the CI-promoter and the functionally linked 5' Barley lectin ER targeting sequence was ligated to a XbaI and EcoRV digested SacB:CTPP:In2-1 plasmid. The complete expression cassette, CIP:Blec:SacB:Blec:In2-1, containing the signals from the Barley lectin gene is sufficient for direction of a protein to the vacuole of the cell was digested with BamHI and KpnI, ligated into the binary vector pZS97K and the resulting plasmid transferred into Agrobacterium by tri-parental mating described in Example 2. Tobacco transformed with the CIP:Blec:SacB:Blec:In2-1 expression cassette inserted into the binary vector was by the methods described in Example 2. Determination of positive transgenic plants which contain the expression vector was by methods previously described (a PCR reaction described in Example 2, and primers specific for the bacterial FTF gene described in Example 3). Induction of the Cl-promoter and expression of the targeted FTF gene was by induction methods described in Example 3. Total RNA extraction and RNA slot blot analysis was by methods described above.

Wild-type tobacco produced no signal on X-ray film exposed to the slot blot filter for up to 48 hours. However, 16 of the 31 transgenic CIP-Blec-SacB-Blec lines tested positive by slot-blot analysis, only in leaves which had been induced with 2-CBSU, as described above. The amount of RNA induced again varied greatly among lines.

The significant phenotype differences demonstrated in CIP-SacB plants compared to the CIP-Spor-SacB or the CIP-Blec-SacB-Blec lines (untargeted FTF expression compared to vacuole targeted FTF expression), suggests that the vacuole targeting signal from either a moncot or a dicotyledenous plant can direct the FTF protein to the vacuole of a tobacco cell. The demonstration of fructan accumulation in damaged leaves of untargeted FTF lines further strengthens the argument that expression of this or enzymes with similar activity in the cytosol of the cell is severely destructive leading to cessation of plant development.

Constitutive Expression of a Vacuole Targeted FTF Gene

Construction the 35S:Spor:SacB:In2-1 Expression Vector

A leaf expression cassette was constructed which contained the 35S CaMV promoter region (Odell et al., Nature 313:810–812 (1985); Hull et al., Virology 86:482–493 (1987)), the translation leader sequence from the chlorophyll a/b binding protein (Cab) gene (Dunsmuir, Nuc. Acids Res., 13:2503–2518 (1985) and the 3' transcription termination region from the nopaline synthase (Nos) gene (Depicker et al., J. Mol. Appl. Genet., 1:561–570 (1982)). The cassette was termed pMH40.

The sporamin vacuole targeting sequence was isolated as a 114 bp BspHI-NcoI DNA fragment from the SK(+)Spor plasmid described above. This 114 bp fragment was ligated into pMH40, which had been digested with NcoI. Because the sporamin vacuole targeting sequence could insert in two possible orientations, several clones were sequenced and one clone containing the 5' to 3' orientation found in the native sporamin protein was designated pMH40:Spor. The plasmid SacB:In2-1 was digested with BamHI and EcoRV and ligated to a DNA fragment containing the CaMV 35S promoter, fused to the vacuole targeting sequence, isolated from pMH40:Spor digested with NcoI, blunt end filled with Klenow enzyme, and finally digested with BamHI. The completed construct was called 35S:Spor:SacB:In2-1. A DNA fragment containing the 35S:Spor:SacB:In2-1 plant expression was isolated by digesting with BamHI and KpnI and ligated into the Binary vector pZS97K. This vector was transferred to Agrobacterium which was then transferred to tobacco was by leaf disk infection described in Example 2. Plants containing the 35S:Spor:SacB:In2-1 expression cassette were identified by producing the expected size DNA fragment in a PCR reaction also described in Example 2. PCR primers specific for the FTF-gene are described in Example 2. Fifteen positive transgenic tobacco lines were placed in soil and allowed to grow to maturity.

Analysis of 35S:Spor:SacB:In2-1 Transformed Plants for the Presence of Fructan

Isolation of large molecular weight carbohydrate polymers from the leaves of 35S:Spor:SacB:In2-1 transformed plants was performed by ethanol precipitation, described in Example 3. The ethanol insoluble extracts were split into two fractions, one was hydrolyzed with 1 M hydrochloric acid at 100° C. for 10 minutes then neutralized with 1 M NaOH. The second fraction was assayed as it was isolated. The two fractions were assayed by TLC methods, described in Example 1.

Wild-type leaves produced no signal in either acid treated or untreated extracts. This data demonstrates that tobacco does not accumulate endogenous fructans. In contrast, 2 of the 4 transformed plants tested, produced a positive signal that did not migrate from the origin on a TLC plate, suggesting the polymer is of large molecular weight. Extracts from the positive plants also produced positive signals in the acid treated lanes which ran the same distance from the origin as did the fructose control. Additional controls of glucose alone or starch spotted on TLC plates, did not produce a positive signal. Chicory fructan treated with HCl or untreated produced the results identical to those of the transgenic tobacco extracts, (i.e., the untreated lanes produced positive signals that did not migrate from the origin and the HCl treated samples produced positive signals that ran the same distance from the origin as did fructose). Collectively, the results demonstrate that a large molecular weight carbohydrate polymer accumulated only in 35S:Spor:SacB:In2-1 transformed plants and the polymer consisted of fructose residues which were released by acid treatment.

Anthrone Analysis of Ethanol Insoluble Extracts

Extracts from the 35S:Spor:SacB:In2-1 transformed plants obtained as described above were incubated at 100° C. with concentrated HCl for 10 minutes, cooled and then neutralized with NaOH. This treatment is sufficient to hydrolyze fructan polymers into individual fructose residues. The HCl treated samples were then assayed for fructose using the quantitative anthrone analysis described in Example 1.

Because the fraction assayed by anthrone was ethanol insoluble, the carbohydrate was determined to be large molecular weight. The results of anthrone analysis indicate that the highest level of fructan accumulated in tobacco with this expression vector was at approximately 1–2% of the dry weight of the leaf.

All but one of the 35S:Spor:SacB:In2-1 transformed plants reached maturity and set seed. Some stunted growth was noted, but the presence of fructan in the otherwise normal plants demonstrates that the vacuole targeted FTF gene is an acceptable method for synthesis and accumulation of this large molecular weight fructose polymer in a transgenic plant.

EXAMPLE 5

Expression of a FTF in Transgenic Potato

Construction of a Potato Tuber Specific, Cytosolic Expression Cassette

The storage protein, patatin promoter was isolated by a PCR reaction (method described in Example 2), using the oligonucleotide primers listed as SEQ ID NO:14 and SEQ ID NO:15. The primers were based on published sequence of a Class I patatin sequence (Rocha-Sosa et al., EMBO J., 8:23–31 (1989). SEQ ID NO:15 also contains the recognition sequence for the enzyme NcoI at the initiation codon.

A 1.0 Kb DNA fragment isolated from the PCR reaction, (using genomic potato DNA as a template) was ligated into the cloning vector pUC18 (New England Biolabs, Beverly, Mass.), digested with SmaI. This plasmid was designated pPPR001. The plasmid pPPR001 containing the patatin promoter region sufficient for tissue specific expression in potato tubers was digested with HindIII and HincII. A 1.0 Kb fragment was isolated and ligated into Bluescript SK(+) and (−) (Stratagene, La Jolla, Calif.) which were digested with HindIII and SmaI. The promoter fragment was recovered in two orientations. The plasmid determined to be in an appropriate orientation for proper expression of the FTF gene was designated PatB.

The PatB plasmid was digested with NcoI and the 5' overhanging nucleotides were blunt end filled with Klenow enzyme. A second digest with BamHI led to the isolation of a 1.0 Kb fragment containing the patatin promoter with an intact initiation codon. This fragment was ligated to the SacB:2-1 plasmid, cut with the BamHI and EcoRV, resulting in the expression cassette PatB:SacB:2-1. Digesting PatB:sacB:2-1 with BamHI and KpnI, isolation of a 2.8 Kb fragment and ligation into pZS97K led to a binary vector containing an expression cassette capable of expressing the FTF gene tissue specifically in transgenic potato tubers. This binary vector was transferred into Agrobacterium as described in Example 2.

Potato Transformation

Transformation of the binary vector into potato was as follows: A leaf disk method was used for transformation of potato with the NPT II gene as the selectable marker. Sterile leaf disks from potato (cultivar Desiree) were co-cultivated with the *Agrobacterium tumefaciens* strain LBA4404 containing the tuber specific FTF expression cassettes inserted into the binary vector pZS97K. Forty-eight hour co-cultivation was under low light in S2 media. Following co-cultivation with Agrobacterium, the leaves were washed with S2 media containing 1 g/L Carbanicillin, dried and placed on S3 media containing 50 mg/L kanamycin. After one week at high light intensity, the leaf disks were transferred to fresh S3 media containing 50 mg/L kanamycin. Small calli formed after 2 weeks on this media and were transferred to S5 media containing 50 mg/L kanamycin for 2–3 additional weeks. Calli developed further during this time period which was then transferred to S7 media containing 50 mg/L kanamycin. During the 2 weeks the calli were on S7 media small shoots developed (about 0.5 cm high). The shoots were excised and placed on rooting media containing 100 µg/L kanamycin. Two weeks following this transfer, the shoots developed to the point where DNA could be extracted from leaves and analyzed by PCR for the presence of the FTF gene, as previously described (Example 2). Primers used in the PCR reaction were specific for the FTF gene (SEQ ID NO:4 and SEQ ID NO:5). Positive lines were then grown in soil for later analysis.

S2 Media
  30 g/L Sucrose
  0.5 g/L MES pH 5.5
  20 g/L mannitol
S3 Media
  200 mg/L glutamine
  0.5 g/L 2-[N-Morpholino]ethanesulfonic acid (MES) (pH 5.7)
  0.5 g/L polyvinyl pyrolidine
  20 g/L mannitol
  20 g/L glucose
  40 mg/L adenine sulphate
  0.5% agarose
  1 mg/L trans-zeatin
  0.1 µg/L Naladixic acid
  1 g/L carbanicillin
S5 Media
  200 mg/L glutamine
  0.5 g/L MES (pH 5.7)
  0.5 g/L polyvinyl pyrolidine
  20 g/L mannitol
  20 g/L glucose
  40 mg/L adenine sulphate
  0.5% agarose
  1 mg/L trans-zeatin
  1 g/L carbanicillin
S7 Media
  200 mg/L glutamine
  0.5./L MES (pH 5.7)
  0.5 g/L polyvinyl pyrolidine
  20 g/L mannitol
  20 g/L glucose
  40 mg/L adenine sulphate
  0.5% agarose
  1 mg/L trans-zeatin
  0.01 µg/L giberillic acid
  1 g/L carbanicillin
Rooting Media
  200 mg/L glutamine
  0.5 g/L MES (pH 5.7)
  0.5 g/L polyvinyl pyrolidine
  20 g/L sucrose
  20 g/L mannitol
  20 g/L glucose
  40 mg/L adenine sulphate
  150 mg/L $CaCl_2$
  0.4% agarose 1 mg/L trans-zeatin
100 mg/L carbanicillin Analysis of Transgenic Potato Plants Transgenic potato lines and untransformed, negative controls were grown in soil to maturity and allowed to produce tubers under cool, low light growth room conditions (12 hour daylength at 22° C. and 12 hours dark at 20° C.)

Phenotypic Analysis of Transgenic Potato Plants

Positive PatB:SacB:2-1, transgenic potato lines, compared to wild-type and transformed negative controls (transformed only with the binary vector pZS97K) displayed dramatically different phenotypes. Young plants transferred into soil were the same size as controls. However, as the plants matured the transgenic lines lagged considerably behind the wild-type. Stunting was variable, but severe in some transgenic lines. At approximately 6–8 weeks after potting in soil, the wild-type and transformed negative controls developed several tubers which varied in size on the same plant. Leaves on the transgenic lines continued to degenerate, developing large necrotic regions. Tubers did not develop on 2 of the 6 transformed plants and were discolored and extremely small on the remaining lines. The majority of the PatB-SacB (untargeted FTF expressors), transgenic lines produced numerous small green tubers, known as aerial tubers, at the base of the plant. Aerial tubers are not true tubers, but represent an outlet for sucrose when carbon transport into the tuber is obstructed. This condition was absent in all control lines. Attempts to regenerate plants from the small transformed tubers failed. Control lines however, produced plants from tubers as expected.

Analysis of Aerial Tubers for the Presence of Fructans

Small green aerial tubers were ground in ethanol as described for the extraction of leaves in Example 3 and treated with HCl or untreated as described in Example 4. Assay for fructan was by TLC (described in Example 1). True tubers from the wild-type and transformed negative control lines produced no detectable signal on TLC plates indicating that true potato tubers do not contain or accumulate endogenous fructan. No transgenic line containing the PatB-SacB construct produced a positive signal on TLC plates.

The extreme stunting, production of aerial tubers and lack of fructan strongly suggests that expression of the FTF gene in the cytosol of developing tuber cells is detrimental to cellular development. The effect may be by preventing sucrose translocation into the immature tuber. Inhibition of tuber cells in this experiment is similar to the results obtained in Example 3 where development of tobacco leaf cells were also inhibited by a cytosolically expressed FTF protein. Several studies (Oparka and Wright, Planta, 175:520–526 (1988), and Oparka and Wright, Planta, 174:123–126 (1988)) have demonstrated that osmotic potential is crucial to tuber development and disruption may retard or inhibit tuber growth by preventing sucrose translocation to developing tubers. The results here are consistent with inhibited development of tubers due to the disruption of sucrose translocation via FTF activity in the cytosol of immature tuber cells.

Construction of a Vacuole Targeted, Tuber Specific FTF Gene

The PatB plasmid was digested with NcoI and blunt end filled with Klenow enzyme, followed by a XhoI digest. The sporamin vacuole targeting sequence was ligated into this plasmid following the isolation of a fragment from the Bluescript(+) subcloning vector containing the sporamin sequence (Example 4), digested with BspHI and XhoI. The resulting plasmid was designated PatB:Spor. PatB:Spor was then digested with NcoI, blunt end filled with Klenow enzyme and digested with a second restriction enzyme, SpeI. Ligated into this was a fragment isolated from SacB:In2-1. The 1.8 Kb fragment was isolated following digestion with SpeI and EcoRV restriction endonucleases. The resulting plasmid was called PatB:Spor:SacB:In2-1. The completed plasmid (PatB:Spor:SacB:In2-1), contained a tuber specific promoter, a vacuole targeting signal operably linked to the FTF coding region and a transcription termination region. This was digested with BamHI and KpnI, the expression fragments isolated, and ligated into the binary vector pZS97K for transformation into Agrobacterium. Transformation into Agrobacterium was by tri-parental mating as described in Example 2. Transformation of potato with this vector was by the methods described above. Positive transformed potato lines were identified by PCR analysis as described in Example 2, using FTF specific primers, described in Example 3. Wild-type potato lines were grown to maturity along with the PatB:Spor:SacB:In2-1 transgenic lines under the conditions described above.

RNA Analysis of PatB:Spor:SacB:In2-1 Transgenic Potato Lines

Total RNA was extracted from developing tubers by the method described for RNA isolation of tobacco leaves in Example 4. Isolated RNAs were separated on 1% agarose gel containing 3% formaldehyde in 5 mM sodium tetraborate, 0.18 mM disodium EDTA. Separated RNAs were transferred to Zetaprobe™ membrane using 20×SSC, the blot hybridized with an appropriate 32P labeled DNA probe fragment (a pB311 EcoRV-XbaI, 1.3 Kb DNA fragment, homologous to the FTF coding region) at 45° C., washed three times with 2×SSC, 0.1% SDS at 25° C., then 3× with 0.1×SSC and 0.1% SDS at 55° C. RNA transcripts from the transformed gene were visualized by exposing the filter to X-ray film for 12–48 hours.

Northern analysis of tubers transformed with the PatB-Spor-SacB (vacuole targeted FTF expressors), construct produced signal when hybridized to the pB311 probe. No signal was found in wild-type tubers or in tubers containing only the binary vector pZS97K. RNA transcript levels varied greatly among transgenic lines.

Fructan Analysis of Tubers Expressing the Spor-SacB Gene

Tubers were ground in ethanol as described for the extraction of large molecular weight carbohydrate from leaves in Example 3. Extracts were treated with HCl by the methods described in Example 4 and assay for fructan was by TLC as described in Example 1. Wild-type tubers and transformed control lines (containing only the binary vector), produced no detectable signal on TLC plates demonstrating again, that potato tubers do not accumulate an endogenous fructan. Two of the 5 PCR positive tubers produced visible signal on a TLC plate which did not migrate from the origin in untreated samples lanes and ran the same distance from the origin as did fructose controls in the acid hydrolyzed samples. Samples of starch untreated or treated with acid did not produce positive signals on TLC plates. This data demonstrates the synthesis and accumulation of large molecular weight fructans in the vacuole of transgenic tuber cells. The presence of fructan in tubers expressing a vacuole targeted SacB FTF gene and the destruction of plants and inhibition of tuber growth when untargeted FTF vectors are transformed into potato clearly indicate that cytosolic expression of this sucrose metabolizing gene is detrimental to plant cells. In contrast to the untargeted FTF transformed tubers, tubers from this experiment, placed in soil germinated, matured and also formed tubers.

EXAMPLE 6

Tissue Specific Expression of a Vacuole Targeted FTF Gene in Maize

The nucleotide sequence of the 10 kD zein gene, including the sequence of the promoter may be found in Kirihara et al., Gene, 71:359–370 (1988). Construction of a corn endosperm specific expression vector utilized in this invention, began by isolating the 5' end of the 10 kD zein gene, including the promoter region and a portion of the coding sequence. This was accomplished using the published sequence to create oligonucleotides for use in a PCR reaction. The oligonucleotides, listed as SEQ ID NO:16 and SEQ ID NO:17, also contain restriction endonuclease recognition sequences for the purpose of cloning the PCR DNA fragment into the cloning vector pTZ18 (Pharmacia, New Brunswick, N.J.). The oligonucleotide SEQ ID NO:16 contains a recognition site for the enzyme EcoRV and SEQ ID NO:17 contains a XbaI recognition site.

A 1.4 Kb DNA fragment from the PCR reaction was recovered, digested with EcoRV and XbaI and subcloned into pTZ18, previously digested with SmaI and XbaI. The resulting plasmid called p10K1, contained the zein nucleotide sequences from –950 to 450, (using the adenosine nucleotide of the translation initiation codon as base 1, (Kirihara et al., Gene, 71:359–370 (1988)).

A second PCR reaction, using oligonucleotides SEQ ID NO:18 and SEQ ID NO:19, produced a 1.39 Kb DNA fragment, consisting of the nucleotides from 1 to 1395. SEQ ID NO:19 contained the recognition site for the endonuclease BamHI and the PCR fragment was digested with BamHI and ligated into the BamHI and SmaI sites of pTZ18. This vector was termed p10K3. The complete zein gene, including the promoter region and coding sequences, were reconstructed from the two plasmids; p10K1 and p10K3 through the use of a unique SpeI restriction enzyme site in each. p10K1 was digested with EcoRI and SpeI and a 994 bp DNA fragment was isolated. This fragment was ligated in to p10K3 digested with the same two enzymes, resulting in the complete zein gene in a vector now termed pCC3. Restriction enzyme sites were further modified, in order to facilitate subcloning fragments into or from this vector. A unique SmaI restriction enzyme site was added at the 5' end of the coding region (1590 bp) by digestion with XbaI and addition of the oligonucleotide sequences, listed as SEQ ID NO:20 AND SEQ ID NO:21. The oligonucleotides were synthesized, phosphorylated, annealed and ligated into pCC3 by standard methods of DNA manipulation.

The 10 kD zein promoter region of this invention was isolated from plasmid pCC3. This was accomplished by digestion of pCC3 with EcoRI followed by a blunt-end filling using Klenow enzyme. The EcoRI filled plasmid was then digested with SmaI and a 923 bp DNA fragment containing the promoter region of the 10 kD Zein gene was isolated and ligated into the plasmid Bluescript SK(+) (Stratagene, La Jolla, Calif.) which was previously digested with HincII. The resulting plasmid, called SK(+)10 kD was digested with NcoI and XhoI. A BspHI and XhoI digested fragment containing the sporamin vacuole targeting sequence isolated from the plasmid SK-Spor, described above, was ligated into the SK(+)10 kD. NcoI-XhoI digested plasmid, resulting in a construct given the name 10 kD-Spor. This plasmid was digested with NcoI, blunt end filled with Klenow enzyme, followed by a second digest with the restriction enzyme SpeI. The DNA fragment containing the corn seed specific promoter operably linked to the sweet potato sporamin vacuole targeting sequence, was isolated and ligated into the plasmid SacB:In2-1, previously digested with SpeI and EcoRV to give the final expression cassette 10 kD-Spor:SacB:In2-1. The cassette was used directly for transformation into corn by particle bombardment.

Transformation of Maize with the Bacterial FTF Gene

Callus cultures were initiated from immature embryos (about 1.5 to 2.0 mm) dissected from kernels derived from crosses of the genotypes A188 and B73, 10 to 12 days after pollination. The embryos were placed with the axis-side facing down and in contact with agarose-solidified N6 medium. The embryos were kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant was cultured on N6 medium and sub-cultured on this medium every 2 to 3 weeks.

The particle bombardment method was used to transfer genes to the callus culture cells. A Biolistic™ PDS-1000/He (DuPont Medical Products) was used for these experiments. A plasmid vector containing a selectable marker gene was used in the transformations. The plasmid, pALSLUC (Fromm et al. Biotechnology, 8:833–839 (1990)), contains a cDNA of the maize acetolactate dehydrogenase synthase (ALS) gene. The ALS cDNA had been mutated in vitro so that the enzyme coded by the gene would be resistant to chlorsulfuron. The change consisted of mutating a tryptophan codon at position 1626 of the cDNA to a leucine codon. The ALS gene is under the control of the CaMV 35S promoter (Odell et al., Nature 313:810–812(1985)) and the 3' region of the nopaline synthase gene from the T-DNA of the Ti plasmid of *Agrobacterium tumefaciens*.

The plasmid pALSLUC was precipitated onto the surface of gold particles. To accomplish this 5 μg of pALSLUC, in Tris-EDTA buffer at a concentration of about 1 μg/μl was added to 50 μl of gold particles (average diameter of 1 μm) suspended in water (60 mg of gold per ml). Calcium chloride (50 μl of a 2.5 M solution) and spermidine (20 μl of a 1.0 M solution) were then added to the gold-DNA suspension as the tube was vortexing. The particles were then centrifuged in a microfuge for 10 seconds and the supernatant removed. The particles were then resuspended in 200 μl of absolute ethanol. The particles were centrifuged again and the supernatant removed. The particles were then resuspended in 30 μl of ethanol. Five μl of the DNA-coated gold particles were then loaded on each macro carrier disk.

Small clusters (2 to 3 mm in diameter) of embryogenic callus was arranged on the surface of agarose-solidified N6 medium contained in a petri dish 12 cm in diameter. The tissue covered a circular area of about 6 cm in diameter. The petri dish containing the tissue was placed in the chamber of the PDS-1000/He. The air in the chamber was then evacuated to a vacuum of 711 mm of Hg. The macrocarrier was accelerated with a helium shock wave using a rupture membrane that bursts when the He pressure in the shock tube reaches 1000 psi. The tissue was placed approximately 8 cm from the stopping screen. Ten plates of tissue were bombarded with the DNA-coated gold particles.

Seven days after bombardment the tissue was transferred to N6 medium that contained 50 mM chlorsulfuron and lacked casein or proline. The tissue continued to grow slowly on this medium. After an additional 2 weeks the tissue was transferred to fresh N6 medium containing chlorsulfuron. After 8 weeks an area of about 1 cm in diameter of actively growing callus was identified on one of the plates containing chlorsulfuron-supplemented medium. This callus continued to grow when sub-cultured on the selective medium. Some of this callus has been transferred to medium that allows plant regeneration.

N6 Medium

| Component | Quantity per liter |
|---|---|
| Solution I | 10.0 ml |
| $CaCl_2$ (1 M) | 1.25 ml |
| Solution III | 10.0 ml |
| $MgSO_4$ (1 M) | 0.75 ml |
| Solution V | 1.0 ml |
| Vitamin Stock | 1.0 ml |
| Casein hydrolysate | 0.1 g |
| Sucrose | 60.0 g |
| Myo-inositol | 0.1 g |
| 2,4-D (2 mg/ml stock) | 0.5 ml |
| pH to 5.8 | |
| Add 6 g of agarose for plates | |
| Solution I | |
| $(NH_4)_2SO_4$ | 23.0 g |
| $KNO_3$ | 141.5 g |
| $KH_2PO_4$ | 20.0 g |
| $H_2O$ | 500.0 ml |
| Solution III | |
| $Na_2EDTA$ | 1.85 g |
| $FeSO_4.7H_2O$ | 1.35 g |
| $H_2O$ | 500.0 ml |
| Solution V | |
| $H_3BO_3$ | 0.16 g |
| $MnSO_4.H_2O$ | 0.33 g |
| $ZnSO_4.7H_2O$ | 0.15 g |
| KI | 0.08 g |
| $Na_2MoO_4.2H_2O$ | 0.025 g |
| $CuSO_4.5H_2O$ | 0.0025 g |
| $CoCl_2.2H_2O$ | 0.0025 g |
| $H_2O$ | 100.0 ml |
| Vitamin Stock | |
| niacin | 0.13 g |
| thiamine | 0.025 g |
| pyridoxine | 0.025 g |
| calcium pantothenate | 0.025 g |
| $H_2O$ | 100.0 ml |

Southern Analysis of Transformed Callus

Southern analysis was performed on callus for the detection of the introduced chimeric FTF gene. Southern analysis was accomplished by isolation of genomic DNA from callus tissue by the DNA extraction methods described in Example 2. DNA was isolated from the transformed callus line or callus derived from the same genotype but that was not transformed, for use as a control. Genomic DNA was digested with BglII. The digested DNA was fractionated by gel electrophoresis through agarose and transferred to a nylon membrane using standard techniques. The nylon blot was hybridized to a nick-translated EcoRV-XbaI DNA fragment isolated from the plasmid pB311. The probe contains only coding sequence from the FTF gene. FTF transformed callus exhibited one dominant band that corresponded to the chimeric gene. Any additional bands of variable molecular weight were presumed to be rearranged copies of the expression cassette.

Southern Analysis of Transgenic Maize Plants

DNA was extracted from mature maize leaves by the extraction method described in Example 2. DNA from untransformed negative control plants and transgenic lines were assayed for the presence of the 10 kD-Spor:SacB:In2-1 expression cassette by PCR analysis using the method and primers described in Example 2 and FTF specific primers, described in Example 3.

In addition, genomic DNA was digested to completion with BglII, separating the fragments on a 1.0% agarose gel, transferring the DNA to Hybond M membrane using 20×SSC and hybridizing the blot with a digoxigenin labeled DNA fragment. The labeled DNA fragment was isolated from the plasmid pB311, by digestion with the restriction enzymes EcoRV and XbaI. This fragment contained only coding sequence from the bacterial FTF gene. Blotting procedures, digoxigenin labeling of probe fragment, hybridization and wash conditions and antibody visualization of signal were as described for the Genius™ blotting kit (USB, Cleveland, Ohio). Southern blotting analyses of the transgenic plants demonstrated multiple inserted copies of intact and rearranged copies of the 10 kD-Spor:SacB:In2-1 cassette. Only those transgenic lines containing an intact cassette were considered positive lines.

Analysis of Transgenic Maize Seed for the Presence of Fructan by TLC 10 kD-Spor:SacB:In2-1 transformed lines were grown in a greenhouse and individual seeds were assayed for the presence of fructan at 30–35 days after pollination or at maturity. Multiple sets of individual seeds from the same transgenic plant were ground in 80% ethanol by the method of carbohydrate extraction described in Example 3. Extracts were treated with HCl by the methods described in Example 5 and samples were determined to contain fructan by analysis on TLC plates described in Example 1. Untransformed control lines did not produce a positive signal for fructan on TLC plates, indicating that corn does not synthesize or accumulate endogenous fructan in seed. Eight of fifteen maize lines tested were positive for fructan by TLC analysis. The PCR and transgenic lines determined to be positive by southern analysis all produced a positive TLC signal. The fructan signal did not migrate significantly from the origin in untreated lanes and ran at the same distance as did the fructose control lane when extracts were heated in acid prior to spotting on a TLC plate. This data demonstrates that a large molecular weight fructose polymer is synthesized and accumulates only in corn seed transformed with the 10 kD-Spor:SacB:In2-1 expression cassette.

Analysis by Anthrone Assay

Mature, dry seed were ground and ethanol insoluble extracts were prepared as described in Example 3. Positive transformed lines and negative control (wild-type corn) extracts assayed by the anthrone method described in Example 5 are summarized in Table 3 below.

TABLE 3

Fructan Accumulation Levels in Transgenic Maize Endosperm Cells Determined By Anthrone Assay
FRUCTOSE
(mg/g fresh weight)
LH 195

| | |
|---|---|
| (control) | 0.0 |
| 1033.8.5 | 2.2 |
| 1033.6.1 | 2.7 |
| 1033.2.1 | 2.1 |

Data from Table 3 demonstrates that fructan accumulates in the ethanol insoluble fraction of corn seeds transformed with the 10 Kd-Spor-SacB (vacuole targeted FTF), expression vector and that the accumulation of fructan in these lines did not prevent development to maturity. Seeds from each line were harvested at maturity, dried and placed in soil. The germination rate of the seed obtained from transformed plants was no different than that demonstrated with seed of untransformed control lines.

EXAMPLE 7

Transgenic Corn Lines Containing Cytosolic or Vacuole Targeted SacB Expression Cassettes Construction of 10 kD-SacB An expression cassette containing the Bacillus SacB gene transcriptionally regulated by a 10 kD zein promoter was constructed by digesting the plasmid pSSU-SacB, described in Example 2, with the restriction enzyme SalI followed by blunt end filling, using Klenow enzyme. A second enzyme digest of the plasmid with NcoI, allowed isolation of a 1.3 kb fragment by agarose gel electrophoresis. The 1.3 kb NcoI/SalI-blunt end filled fragment was ligated into the plasmid pCC3 (described in Example 6) which had previously been digested with NcoI and SmaI. The resulting recombinant plasmid was designated 10 kD-SacB.

The completed expression cassette, 10 kD-SacB, containing the 10 kD zein promoter, sufficient for tissue and developmental specific expression of the SacB gene in the cytosol of endosperm cells, was used directly for transformation into corn by particle bombardment, described in Example 6.

Phenotypic Characterization of Transgenic Seed Containing the 10 kD-SacB Expression Cassette Transgenic corn lines containing the 10 kD-SacB cassette were grown under greenhouse conditions and self-pollinated. Phenotypically, transgenic corn seed containing the 10 kD-SacB cassette were not easily distinguished from wild-type kernels early in development (10–15 days after pollination). However, mature seed displayed a severely shrunken phenotype, dramatically different than wild-type seed (transgenic kernels that did not contain the 10 kD-SacB cassette) on the same ear. The difference in seed weight is demonstrated in Table 4 below.

Analysis of Transgenic Seed Containing the 10 kD-SacB Expression Cassette

Transgenic and wild-type seed analyzed for the presence of fructan were collected at maturity (approximately 45–55 days after pollination). Several seeds displaying normal dent or shrunken phenotypes were assayed for fructan by the TLC method described in Example 1. Only seed with a shrunken phenotype produced a positive signal on a TLC plate stained with urea-phosphoric acid. The positive fructan signal did not migrate from the origin on the TLC plate, suggesting a polymer of high molecular weight.

Quantitative analysis of fructan in seed demonstrating dent and shrunken phenotypes was performed by the anthrone method described in Example 5. Seed weight and per cent fructan based on the dry weight of the seed is listed in Table 4.

TABLE 4

| Seed Line | Seed Weight (mg) | % Fructose (seed dry wt.) |
|---|---|---|
| 654#1 | 30 | 1.19 |
| 654#2 | 30 | 2.38 |
| 654#3 | 20 | 0.71 |
| 654#4 | 40 | 2.17 |
| 654#5 | 20 | 1.25 |
| 654#6 | 270 | 0.23 |
| 654#7 | 220 | 0.36 |
| 654#8 | 240 | 0.16 |

Analysis by TLC and data in Table 4 demonstrate that seeds with a dent phenotype (654# 6,7 and 8), did not accumulate fructan and only in seeds with a severe shrunken phenotype (654# 1 through 5) synthesized this polymer. It appears from this data, that cytosolic expression of the SacB gene in corn endosperm dramatically affects endosperm development. Endosperm development may be affected by decreased accumulation of dry matter in seed containing the 10 kD-SacB cassette. Although starch was present in seed containing fructan (judged by staining with iodine), the amount of starch was considerably less considering the 10-fold loss in seed weight.

Germination of Seed Containing the 10 kD-SacB Cassette

Fifteen seeds displaying the shrunken phenotype were placed in metro-mix soil and allowed to germinate under greenhouse conditions. During a 3 week period, only one of the fifteen seeds germinated (0.067% germination rate). The one small shoot (3.7 cm) did not appear vigorous and did not survive past 2–3 days. In contrast to soil, 10 transgenic seeds geminated on solid media containing sucrose (#64 media) produced 3 shoots (30% germination). All 3 shoots developed normally, reached maturity and set seed.

The results of 10 kD-SacB germination assays strongly suggest that accumulation of fructan in the cytosol of endosperm-tissue alters development of the seed, possibly by inhibiting accumulation of nutrients (especially carbohydrate) in the seed. The result is a severe reduction in germination rate and seedling viability.

64 Media

| Component | Quantity per liter |
|---|---|
| Schenk and Hildebrandt basal salts (Sigma #S6765) | 1.6 g |
| Nitsch and Nitsch vitamin stock (Sigma #N0390) | 1.0 ml |
| Sucrose | 10.27 g |

Construction of 10 kD-Blec-SacB

An expression cassette containing the Bacillus SacB gene functionally linked to the N and C-terminal barley lectin ER and vacuole targeting sequences, operably linked to the 10 kD zein gene promoter was constructed by first adding the C-terminal, vacuole targeting sequence to the plasmid SacB:In2-1, resulting in the plasmid SacB:CTPP:In2-1 described in Example 4.

The N-terminal signal from barley contained in the plasmid SK-5' BLEC, described in Example 4 was fused to the 10 kD zein promoter contained in the plasmid pCC3 (described in Example 6). This was accomplished by digesting SK-5' BLEC with the enzymes BspHI and XhoI. The fragment isolated from this digest was ligated into pCC3, digested with NcoI and XhoI, resulting in the plasmid pCC3-BLEC. The expression cassette was completed by digesting pCC3-BLEC with NcoI and blunt end filled using Klenow enzyme. The DNA was precipitated, reusspended in water and redigested using XbaI as described in Example 4. Isolation of a fragment containing the 10 kD zein promoter functionally linked to the 5' barley lectin ER signal was ligated to the plasmid SacB:CTPP:In2-1 previously digested with XbaI and EcoRV, resulting in the final expression cassette, 10 kD-BLEC-SacB.

The completed expression cassette, 10 kD-BLEC-SacB, containing the tissue and developmental specific 10 kD zein promoter in addition to the ER and vacuole sorting signals from Barley lectin is sufficient for direction of the SacB protein to the vacuole of a cell. The cassette was used directly for transformation into corn by particle bombardment as described in Example 6.

Qualitative Analysis of Transgenic Maize Seed for the Presence of Fructan by TLC Assay 10 kD-BLEC-SacB transformed lines were grown in a greenhouse and individual seeds were assayed for the presence of fructan at 30–35 days after pollination or at maturity (45–55 days after pollination). Multiple seeds from several regenerated lines were assayed for the presence of fructan by TLC assay described in Example 1. Two of the six corn lines tested produced a positive signal which did not migrate from the origin on a TLC plate, suggesting the fructose polymer is large molecular weight.

Germination of Transgenic Seed Containing the 10 kD-BLEC-SacB Cassette

Seed containing the 10 kD-BLEC-SacB cassette were placed in metro-mix soil and germinated under greenhouse conditions. Of the 35 seed planted, 29 germinated (83% germination rate), developed to maturity and produced R2 seed containing fructan. No differences were observed, between transgenic seed and wild-type, dent lines, with respect to germination rate, seedling vigor or seed set.

Quantitative Analysis of Fructan Positive 10 kD-BLEC-SacB in Transformed Corn

Ten mature seeds from one of the two positive lines were individually tested for fructan concentration by the anthrone method described in Example 5. Seed from this line segregates for the SacB gene therefore, as expected, some will not accumulate fructan. Negative seed serves as an internal control in this experiment.

Four mature seed from wild-type (dent corn) were also included as negative controls. The data is summarized in Table 5 below.

TABLE 5

Quantitative Measurement of Fructan in 10 kD-BLEC-SacB Transformed Corn Lines and Controls
% FRUCTAN (based on seed dry weight)

| | |
|---|---|
| Dent seed#1 | 0.06 |
| Dent seed#2 | 0.00 |
| Dent seed#3 | 0.04 |
| Dent seed#4 | 0.23 |
| 10 kD BLEC SacB | |
| 625#1 | 0.12 |
| 625#2 | 0.28 |
| 625#3 | 0.29 |
| 625#4 | 0.88 |
| 625#5 | 0.28 |
| 625#6 | 0.33 |
| 625#7 | 0.26 |
| 625#8 | 1.35 |
| 625#9 | 0.20 |
| 625#10 | 1.94 |

The data in Table 5 demonstrates that fructan accumulation in seed containing the 10 kD-BLEC-SacB expression cassette is equivalent to the level found in transformed corn lines containing the 10 kD:Spor:In2-1 cassette (fructan levels listed in Table 3, Example 6). The result suggests that targeting of the SacB gene to the vacuole of endosperm is accomplished and that the receptor(s) responsible for directing protein to the vacuole of corn endosperm recognize both monocot and dicot targeting signals.

Information in this Example demonstrates that accumulation of large molecular weight fructan in the cytosol of transgenic corn endosperm is detrimental to the development of that seed, inhibiting germination and seedling vigor. Fusion of vacuole targeting signals (either monocot or dicot signals), to the SacB protein relieves the detrimental effect. Vacuole targeted SacB protein synthesizes fructan without effect on development, germination or seedling viability, nor does the presence of fructan impair the ability to pass this trait on to progeny.

EXAMPLE 8

Enhanced Fructan Accumulation in High Sugar Corn Lines

Numerous mutant corn lines have been described, often isolated because of varied physical properties of the seed, such as altered translucence or kernel shape compared to a wild-type "dent" also known as "field corn". Several mutant lines producing a "shrunken" kernel have been characterized and found to contain lower levels of starch, but increased concentration of soluble sugars (reviewed in Doehlert, and Min Kuo, Plant Cell Physiol., 35:411–418 (1994)). The biochemical lesions are not always clear, as in the mutant lines such as shrunken-4 (sh4) or sugary/sugary enhancer (su/se). However, the mutant allele has been well characterized and the genes cloned for several mutants including shrunken-1 (sh1), shrunken-2 (sh2) and brittle-2 (bt2) (McCarty et. al., Proc. Natl. Acad. Sci. (USA), 83:9099–9103 (1986), Bhave et. al., The Plant Cell, 2:581–588 (1990)). Although mutations occur at various steps in the starch biochemical pathway, decreased starch accumulation and increased soluble sugars, including sucrose, is often the consequence. The level of blockage in the pathway and therefore, the concentration of soluble sugars varies with the mutant line.

Expression of the bacterial SacB gene in a homozygous starch mutant line results in an increased level of fructan accumulation due to the larger available substrate pool. Expression of the SacB gene in the mutant line may be accomplished by direct transformation or through traditional breeding of a mutant line with a transgenic corn line containing a SacB expression cassette, such as that described in Examples 6 and 7. Mutant corn lines containing the SacB gene in this Example were produced by genetic crosses of a "dent" line containing the 10 kD-Spor:SacB:In2-1 expression vector with the mutants sh1, sh2, sh4 and su/se. The transgenic SacB line contains a wild-type allele at the sh1, sh2, and su/se locus therefore, the F1 seed from the original cross was "selfed" resulting in F2 seed segregating for the SacB gene together with homozygous and heterozygous mutant alleles. Seed homozygous for the starch pathway mutation was easily identified by the shriveled or shrunken phenotype. Individual kernels segregating for shrunken and normal phenotypes were selected for quantitative fructan analysis by the anthrone method described in Example 5. Results of the anthrone analysis are listed in Table 6 below.

TABLE 6

| 202.1 SacB-Dent | 4094-1.128 SacB-sh4 | 4092-1.20 SacB-sh2 | 4097-4.46 SacB-su | 4089-4.68 SacB-sh1 |
|---|---|---|---|---|
| 1.53 | 0.32 | 1.85 | 2.18 | 4.82 |
| 2.22 | 0.39 | 10.09 | 1.59 | 0.41 |
| 2.90 | 0.13 | 13.98 | 1.55 | 5.75 |
| 0.48 | 0.21 | 6.93 | 3.26 | 3.07 |
| 0.10 | 0.22 | 0.23 | 4.43 | 0.39 |
| 1.43 | 0.00 | 9.23 | 2.06 | 0.38 |
| 0.00 | 0.23 | 0.40 | 2.68 | 1.44 |
| 1.19 | 0.33 | 2.17 | 5.01 | 0.40 |
| 0.11 | 0.26 | 7.80 | 2.16 | 0.33 |
| 0.00 | 0.24 | 7.81 | 1.22 | 3.00 |
| 1.52 | 0.04 | 0.91 | 1.25 | 0.36 |
| 0.00 | 0.00 | 6.81 | 1.41 | 1.10 |
| 1.36 | 0.22 | 10.70 | 0.72 | 1.47 |
| 0.00 | | 8.61 | 0.71 | 0.97 |
| 2.77 | | 2.92 | 8.69 | 0.92 |

Information in Table 6 suggests that fructan accumulation may be altered by expressing the SacB gene in various corn lines. The mutant line 4094.1.128 does not accumulate fructan at levels similar to that demonstrated for SacB in dent lines (see Examples 6 and 7), suggesting the genetic lesion in this line may also affect SacB expression. Evidence for this is discussed in Doehlert and Min Kuo, Plant Cell Physiol., 35: 411–418 (1994). The genetic lesion in the sh4 line, leading to increased sucrose levels, is believed to involve pyridoxyl phosphate metabolism. The result is a general reduction of protein synthesis in developing kernels. Doehlert and Min Kuo also demonstrate that transcript and protein levels in sh4 seed are significantly reduced. The SacB gene in the sh4 corn line described here, is driven by a zein promoter. The decreased level of zein expression in this mutant would result in lower levels of SacB protein and could explain why increased fructan is not present in this line even though sucrose levels are reported to be higher than found in dent lines.

Line 4092-1.20, segregates for homozygous and heterozygous sh2 allele and the SacB gene. Sucrose levels in sh2 lines are reported to be the highest among the mutant lines tested in this Example (Doehlert and Min Kuo, Plant Cell Physiol., 35: 411–418 (1994)). Data in Table 6 demonstrates that the SacB gene in this background accumulates the highest level of fructan. Line 4097-4.26 and line 4089-4.68 segregate for homozygous and heterozygous su and sh1 alleles, respectively. They also segregate for the SacB gene. The su and sh1 lines accumulate similar, but higher levels of sucrose compared to wild-type endosperm. Table 6 demonstrates that they accumulate higher levels of fructan compared to dent corn lines containing the SacB gene, but less than that found in the sh2 background.

With the exception of mutant line sh4 (explained above), individual seeds from starch mutant lines containing the SacB gene listed in Table 6 demonstrate that fructan accumulation was greater in corn lines containing a genetic block in the starch biosynthetic pathway. Increased sucrose in the cytosol, due to the genetic block, equilibrates with the vacuole in the mutant line resulting in an increase in fructan synthesis. Although it may be obvious that increased sucrose in the vacuole of a cell containing a vacuole targeted SacB protein would lead to increased fructan levels, the data in this Example clearly demonstrate that altering fructan levels in corn endosperm may also be accomplished by altering sucrose in the cytosol of the cell. Increasing sucrose levels may be accomplished by several means (e.g. overexpression or antisense of sucrose metabolic genes) or in this Example by expression of the SacB gene in a mutant line deficient in starch synthesis.

What is claimed is:

1. A recombinant DNA construct comprising a tissue specific promoter, operably linked to a vacuole targeting sequence, operably linked to a coding sequence for a bacterial levansucrase gene wherein transformation of a plant cell selected from the group consisting of corn, potato, and tobacco with said construct results in production of fructan in the vacuole of said plant cell.

2. A plant selected from the group consisting of corn, potato, and tobacco transformed with the construct of claim 1 such that said plant produces fructan which accumulates in the vacuole of the cells of the plant.

3. A method of producing fructan comprising growing the plant of claim 2, harvesting said plant, and extracting said fructan from the harvested plant.

4. A recombinant DNA construct as described in claim 1 wherein the tissue specific promoter is specific to seed.

5. A recombinant DNA construct as described in claim 1 wherein the tissue specific promoter is specific to tubers.

6. A plant transformed with the construct of claim 4 wherein the plant produces fructan which accumulates in the seed.

7. A plant transformed with the construct of claim 5 wherein the plant produces fructan which accumulates in the tuber.

8. A method of increasing fructan levels in plants, comprising transforming a plant cell that has a higher than native sucrose level with a recombinant DNA construct comprising a tissue specific promoter, operably linked to a vacuole targeting sequence, operably linked to a coding sequence of a bacterial levansucrase gene, and growing a fertile, sexually mature, transformed plant from the transformed plant cell, wherein the transformed plant synthesizes and accumulates fructan.

9. A transformed plant produced by the method of claim 8.

10. A seed produced by the transformed plant of claim 9.

11. The method of claim 8 wherein the transformed plant is corn.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: single
      (D) TOPOLOGY: linear (ii) MOLECULE TYPE: cDNA (iii) HYPOTHETICAL: No (iv) ANTI-SENSE: No (ix) FEATURE:
      (A) NAME/KEY: misc_feature
      (B) LOCATION: 1..31
      (D) OTHER INFORMATION: /product= "synthetic oligomer"

(xi) SEQUENCE DESCRIPTION: SEQ ID NO:1:

CTTCGCGAAG AAGATATCAA TAACCAAAAG C      31

(2) INFORMATION FOR SEQ ID NO:2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: cDNA (iii) HYPOTHETICAL: No (iv) ANTI-SENSE: No (ix) FEATURE:
      (A) NAME/KEY: misc_feature (B) LOCATION: 1..21
            (D) OTHER INFORMATION: /product= "Synthetic
                Oligomer"

(xi) SEQUENCE DESCRIPTION: SEQ ID NO:2:

GAAGTTTGAA TCTTGAGATC T                                              21

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..32
        (D) OTHER INFORMATION: /product= "Synthetic
            Oligomer"

(xi) SEQUENCE DESCRIPTION: SEQ ID NO:3:

TCTAGAGATA TCCATGGTTA ATTACACTTA GA                                  32

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..21
        (D) OTHER INFORMATION: /product= "Synthetic
            Oligomer"

(xi) SEQUENCE DESCRIPTION: SEQ ID NO:4:

ACGTACGGCG TCTCTCATAT T                                              21

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..24
        (D) OTHER INFORMATION: /product= "Synthetic
            Oligomer"

(xi) SEQUENCE DESCRIPTION: SEQ ID NO:5:

```
GTCGACTTAG TTGACTGTCA GCTG                                           24

(2) INFORMATION FOR SEQ ID NO:6:

(i) SEQUENCE CHARACTERISTICS:
        (A) LENGTH:  137 base pairs
        (B) TYPE:  nucleic acid
        (C) STRANDEDNESS:  single
        (D) TOPOLOGY:  linear (ii) MOLECULE TYPE:  cDNA (iii) HYPOTHETICAL:  No (iv) ANTI-SENSE:  No (ix) FEATURE:
        (A) NAME/KEY:  misc_feature
        (B) LOCATION:  1..137
        (D) OTHER INFORMATION:  /product= "Synthetic
            Oligomer"

(xi) SEQUENCE DESCRIPTION:  SEQ ID NO:6:

ACTAGTACCT GCGATCATGA AAGCCCTCAC ACTCGCTCTC TTCTTAGCTC TTTCCCTCTA    60

TCTCCTGCCC AACCCAGCTC ATTCTAGGTT CAATCCAATC AGGCTTCCAA CCACACACGA   120

ACCCGCCATG GCTCGAG                                                 137

(2) INFORMATION FOR SEQ ID NO:7:

(i) SEQUENCE CHARACTERISTICS:
        (A) LENGTH:  137 base pairs
        (B) TYPE:  nucleic acid
        (C) STRANDEDNESS:  single
        (D) TOPOLOGY:  linear (ii) MOLECULE TYPE:  cDNA (iii) HYPOTHETICAL:  No (iv) ANTI-SENSE:  No (ix) FEATURE:
        (A) NAME/KEY:  misc_feature
        (B) LOCATION:  1..137
        (D) OTHER INFORMATION:  /product= "Synthetic
            Oligomer"

(xi) SEQUENCE DESCRIPTION:  SEQ ID NO:7:

CTCGAGCCAT GGCGGGTTCG TGTGTGGTGG GGAGGCGGAT GGGATTGAAC CTGGAATGGG    60

CTGGATTGGG CAGGAGATAG AGGGAAAGAG CTAAGAAGAG AGCGAGTGTG AAGGCTTTCA   120

TGATCGCAGG TACTAGT                                                 137

(2) INFORMATION FOR SEQ ID NO:8:

(i) SEQUENCE CHARACTERISTICS:
        (A) LENGTH:  39 amino acids
        (B) TYPE:  amino acid
        (C) STRANDEDNESS:  single
        (D) TOPOLOGY:  linear (ii) MOLECULE TYPE:  peptide (iii) HYPOTHETICAL:  No (iv) ANTI-SENSE:  No (ix) FEATURE:
        (A) NAME/KEY:  Peptide
        (B) LOCATION:  1..38
```

5,908,975

61

62

-continued (xi) SEQUENCE DESCRIPTION: SEQ ID NO:8:

Met Lys Ala Leu Thr Leu Ala Leu Phe Leu Ala Leu Ser Leu Tyr Leu
1               5                  10                  15

Leu Pro Asn Pro Ala His Ser Arg Phe Asn Pro Ile Arg Leu Pro Thr
            20                  25                  30

Thr His Glu Pro Ala Met Pro
        35

(2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..56
        (D) OTHER INFORMATION: /product= "Synthetic
            Oligomer"

(xi) SEQUENCE DESCRIPTION: SEQ ID NO:9:

AGGTCTACG CCGAGGCCAT CGCCGCCAAC TCCACTCTTG TCGCAGAATG AGATCT      56

(2) INFORMATION FOR SEQ ID NO:10:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..56
        (D) OTHER INFORMATION: /product= "Synthetic
            Oligomer"

(xi) SEQUENCE DESCRIPTION: SEQ ID NO:10:

AGATCTCATT CTGCGACAAG AGTGGAGTTG GCGGCGATGG CCTCGGCGTA GACCTC      56

(2) INFORMATION FOR SEQ ID NO:11:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: No (iv) ANTI-SENSE: No (ix) FEATURE:
        (A) NAME/KEY: Peptide
        (B) LOCATION: 1..15
        (D) OTHER INFORMATION: /label= Peptide (xi) SEQUENCE DESCRIPTION: SEQ ID NO:11:

Val Tyr Ala Glu Ala Ile Ala Ala Asn Ser Thr Leu Val Ala Glu Pro
1               5                   10                  15

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..38
        (D) OTHER INFORMATION: /product= "Synthetic
            Oligomer"

(xi) SEQUENCE DESCRIPTION: SEQ ID NO:12:

CTAACAGAAT TCATCATGAA GATGATGAGC ACCAGGGC         38

(2) INFORMATION FOR SEQ ID NO:13:

(i) SEQUENCE CHARACTERISTICS:
        (A) LENGTH: 38 base pairs
        (B) TYPE: nucleic acid
        (C) STRANDEDNESS: single
        (D) TOPOLOGY: l inear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..38
        (D) OTHER INFORMATION: /product= "Synthetic
            Oligomer"

(xi) SEQUENCE DESCRIPTION: SEQ ID NO:13:

GTCGACCATG GTCTGGGCGT GCGCGGTGCG GCGGCGGA         38

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..20
        (D) OTHER INFORMATION: /product= "Synthetic
            Oligomer"

(xi) SEQUENCE DESCRIPTION: SEQ ID NO:14:

TTGTAGTTAA TGCGTATTAG         20

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..22
        (D) OTHER INFORMATION: /product= "Synthetic
            Oligomer"

(xi) SEQUENCE DESCRIPTION: SEQ ID NO:15:

CCATGGTGCA AATGTTCAAA GT                      22

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..25
        (D) OTHER INFORMATION: /product= "Synthetic
            Oligomer"

(xi) SEQUENCE DESCRIPTION: SEQ ID NO:16:

TGACATACC ATCATATTTG ATATC                    25

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: No (iv) ANTI-SENSE: No (ix) FEATURE:
        (A) NAME/KEY: misc_feature
        (B) LOCATION: 1..30
        (D) OTHER INFORMATION: /product= "Synthetic
            Oligomer"

(xi) SEQUENCE DESCRIPTION: SEQ ID NO:17:

TTCTATCTAG AATGCAGCAC CAACAAAGGG              30

(2) INFORMATION FOR SEQ ID NO:18:

(i) SEQUENCE CHARACTERISTICS:

(A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: No (iv) ANTI-SENSE: No (ix) FEATURE:
            (A) NAME/KEY: misc_feature
            (B) LOCATION: 1..30
            (D) OTHER INFORMATION: /product= "Synthetic
                Oligomer"

(xi) SEQUENCE DESCRIPTION: SEQ ID NO:18:

ATGGCAGCCA AGATGCTTGC ATTGTTCGCT                                        30

(2) INFORMATION FOR SEQ ID NO:19:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: cDNA (iii) HYPOTHETICAL: No (iv) ANTI-SENSE: No (ix) FEATURE:
            (A) NAME/KEY: misc_feature
            (B) LOCATION: 1..32
            (D) OTHER INFORMATION: /product= "Synthetic
                Oligomer"

(xi) SEQUENCE DESCRIPTION: SEQ ID NO:19:

GACTCGGATC CAGCTGAGAA TTAGGAGCCT TG                                     32

(2) INFORMATION FOR SEQ ID NO:20:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: cDNA (iii) HYPOTHETICAL: No (iv) ANTI-SENSE: No (ix) FEATURE:
            (A) NAME/KEY: misc_feature
            (B) LOCATION: 1..13
            (D) OTHER INFORMATION: /product= "Synthetic
                Oligomer"

(xi) SEQUENCE DESCRIPTION: SEQ ID NO:20:

CTAGCCCGGG TAC                                                          13

(2) INFORMATION FOR SEQ ID NO:21:

(i) SEQUENCE CHARACTERISTICS:
            (A) LENGTH: 13 base pairs
            (B) TYPE: nucleic acid
            (C) STRANDEDNESS: single
            (D) TOPOLOGY: linear

```
    (ii) MOLECULE TYPE:  cDNA (iii) HYPOTHETICAL:  No (iv) ANTI-SENSE:  No (ix) FEATURE:
         (A) NAME/KEY:  misc_feature
         (B) LOCATION:  1..13
         (D) OTHER INFORMATION:  /product= "Synthetic
             Oligomer"

(xi) SEQUENCE DESCRIPTION:  SEQ ID NO:21:

CTAGGTACCC GGG                                                              13
```